(12) United States Patent
Erdmann et al.

(10) Patent No.: US 10,087,199 B2
(45) Date of Patent: Oct. 2, 2018

(54) SUPER-RESOLUTION IMAGING COMPOSITIONS AND METHODS USING SAME

(71) Applicant: Yale University, New Haven, CT (US)

(72) Inventors: Roman Erdmann, New Haven, CT (US); Alanna Schepartz Shrader, New Haven, CT (US); Derek Toomre, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 14/919,216

(22) Filed: Oct. 21, 2015

(65) Prior Publication Data

US 2016/0115180 A1      Apr. 28, 2016

Related U.S. Application Data

(60) Provisional application No. 62/067,043, filed on Oct. 22, 2014.

(51) Int. Cl.
| | | |
|---|---|---|
| *C07F 7/08* | (2006.01) | |
| *A61K 49/00* | (2006.01) | |
| *C07C 271/34* | (2006.01) | |
| *G01N 33/58* | (2006.01) | |
| *C09B 11/28* | (2006.01) | |
| *C09B 57/00* | (2006.01) | |

(52) U.S. Cl.
CPC ........ *C07F 7/0807* (2013.01); *A61K 49/0021* (2013.01); *A61K 49/0052* (2013.01); *C07C 271/34* (2013.01); *C07F 7/0816* (2013.01); *C09B 11/28* (2013.01); *C09B 57/00* (2013.01); *G01N 33/582* (2013.01); *C07C 2601/18* (2017.05)

(58) Field of Classification Search
CPC ........ C07F 7/088; C07C 271/34; A61K 51/00
See application file for complete search history.

(56) References Cited

U.S. PATENT DOCUMENTS

| | | | |
|---|---|---|---|
| 5,543,390 A | * | 8/1996 | Yatvin .................... A61K 9/167 424/450 |
| 8,547,533 B2 | | 10/2013 | Knutson et al. |
| 2013/0302246 A1 | | 11/2013 | Hilderbrand et al. |

FOREIGN PATENT DOCUMENTS

JP          2014157150 A        8/2014

OTHER PUBLICATIONS

Fabien Emmetiere et al. 18F-Labeled-Bioorthogonal Liposomes for In vivo Targeting, Bioconjugate Chemistry, 2013, 24, 1784-1789.*
"NBD-and BODIPY Dye-Labeled Sphingolipids", Molecular Probes, Product Information, Jul. 25, 2003.
"Tetrazine-TCO Ligation Chemistry", Kerafast, Product Information. Retrieved from Internet on Feb. 20, 2016. <URL: http://www.kerafast.com/c-472-tetrazine-tco-ligation-chemistry.aspx?gcl>.
Devaraj, et al., "Biomedical Applications of Tetrazine Cycloadditions", Acc Chem Res. 44(9), Sep. 20, 2011, 816-827.
Erdmann, et al., "High-Density Lipid Probe for Live Nanoscopy of the Golgi", Yale University; Department of Cell Biology, Department of Chemistry, Dec. 14, 2013, (Poster).
Knall, et al., "Inverse electron demand Diels-Alder (iEDDA)-initiated conjugation: a (high) potential click chemistry scheme", Chem Soc Rev. 42(12), Jun. 21, 2013, 5131-5142.
Lukinavičius, et al., "A near-infrared fluorophore for live-cell super-resolution microscopy of cellular proteins", Nat Chem. 5(2), Feb. 2013, 132-139.

* cited by examiner

*Primary Examiner* — Michael G Hartley
*Assistant Examiner* — Jagadishwar Rao Samala
(74) *Attorney, Agent, or Firm* — Saul Ewing Arnstein & Lehr LLP; Kathryn Doyle; Domingos J. Silva

(57) ABSTRACT

The invention provides compositions that may be used for imaging intracellular structures. The invention further provides methods of imaging intracellular structures. In certain embodiments, the compositions of the invention include trans-cyclooctene-containing ceramide lipids and tetrazine-containing rhodamine-related dyes.

8 Claims, 14 Drawing Sheets

Fig. 2A
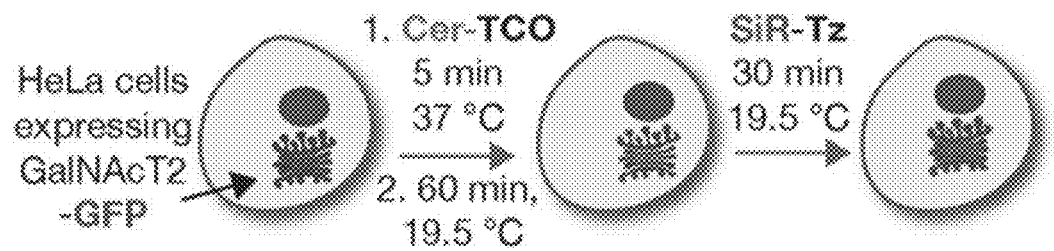
Fig. 2B
green (GFP)
Fig. 2C
red (SiR)
Fig. 2D
merge
+ SiR-Tz
− Cer-TCO
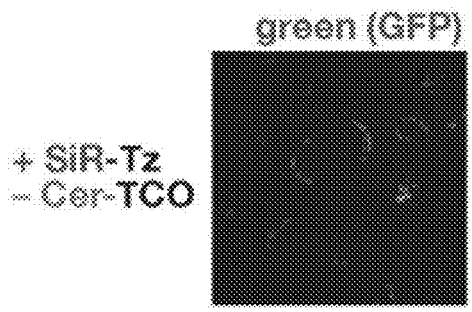
+ SiR-Tz
+ Cer-TCO
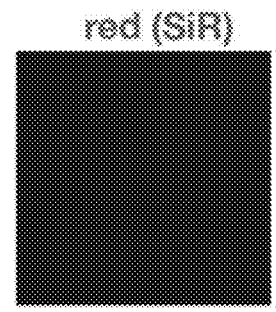
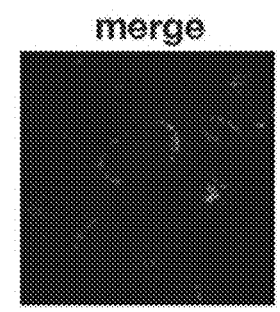
— 20 μm time lapse STED DPBS buffer (pH 7.4)

DPBS buffer (pH 7.4) + 0.1% SDS

• SiR-OH
• SiR-Tz
• SiR-TCO
• Cer-SiR

|  | DPBS pH 7.4 | | | DPBS pH 7.4 + 0.1 % SDS | | |
| --- | --- | --- | --- | --- | --- | --- |
|  | $\lambda_{abs}/\lambda_{em,max}$ [nm] | $\varepsilon_{max}$ [$M^{-1} \cdot cm^{-1}$] | $F_{rel.}$ | $\lambda_{abs}/\lambda_{em,max}$ [nm] | $\varepsilon_{max}$ [$M^{-1} \cdot cm^{-1}$] | $F_{rel.}$ |
| SiR-OH | 645/654 | 188000 | 100 | 645/654 | 161000 | 100 |
| SiR-Tz | 649/656 | 8000 | 2.2 | 649/660 | 48000 | 23 |
| SiR-TCO | nd/656 | <2000 | 3.4 | 650/660 | 41000 | 19 |
| Cer-SiR | nd/658 | <2000 | 0.9 | 650/659 | 51000 | 24 |

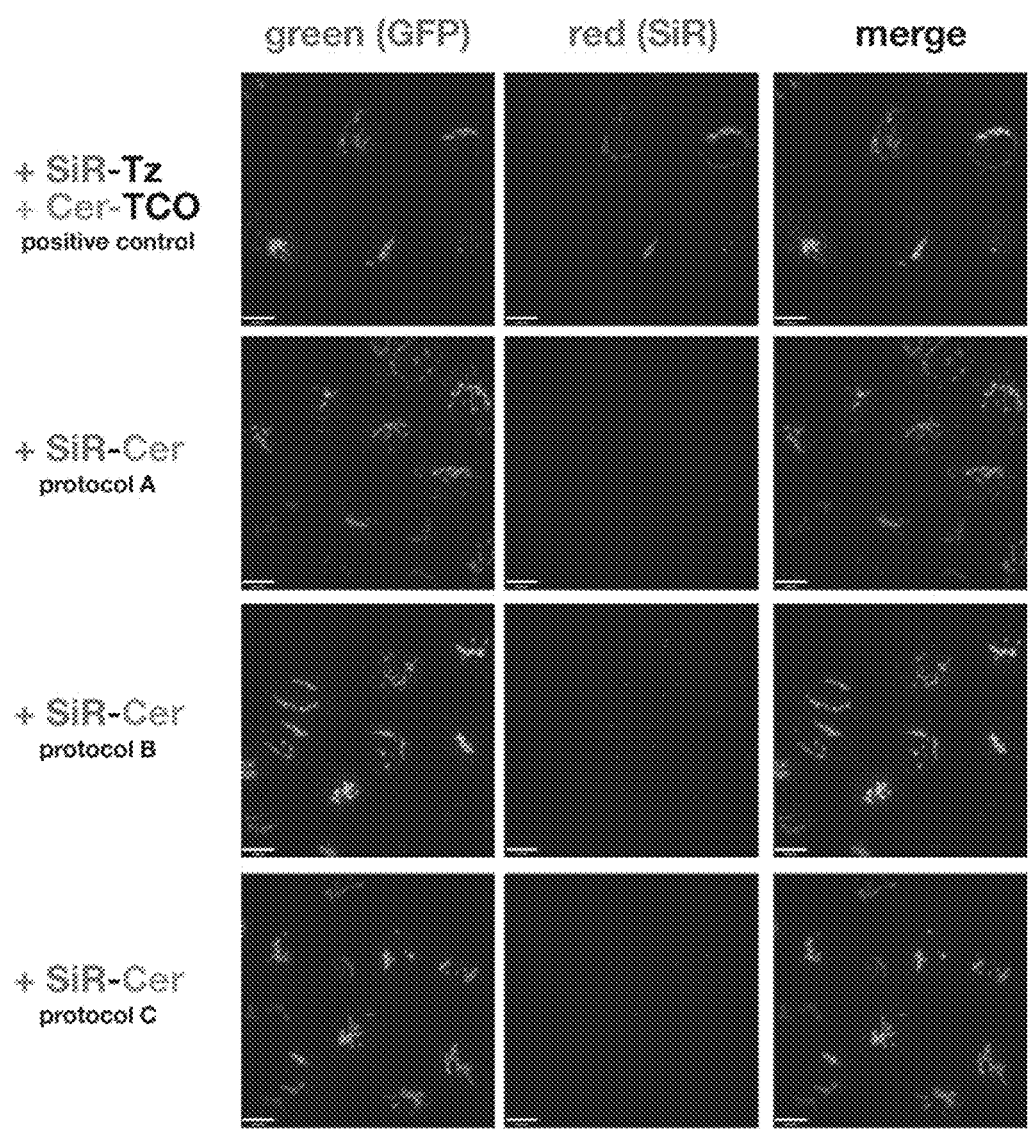

SUPER-RESOLUTION IMAGING COMPOSITIONS AND METHODS USING SAME

CROSS-REFERENCE TO RELATED APPLICATIONS

The present application claims priority under 35 U.S.C. 119(e) to U.S. Provisional Application No. 62/067,043, filed Oct. 22, 2014, all of which is hereby incorporated by reference in its entirety herein.

STATEMENT REGARDING FEDERALLY SPONSORED RESEARCH OR DEVELOPMENT

This invention was made with government support under GM83257 awarded by National Institutes of Health. The government has certain rights in the invention.

BACKGROUND OF THE INVENTION

Super-resolution "nanoscopes" can dramatically increase the resolving power of light microscopes, revealing novel details of organelle structure, function and dynamics in living cells. Nevertheless, the complex requirements for nanoscopy pose real challenges for both fluorophore design and labelling logic. The fluorophore must be bright, photostable and live cell-compatible, and the labelling method must yield a high fluorophore density that is benign to organelle function. As nanoscopes push the resolution envelope to tens of nanometers, there is a critical need for high density probes that demark organelle boundaries with sufficient photostability to study organelle dynamics.

While most nanoscopy applications rely on labelled proteins, lipids represent a complementary attractive target, as they are present at approximately a hundred-fold higher density and their organization defines the de facto boundary of the organelle. Commercially available fluorescent lipids, such as BODIPY® FL C5-ceramide, are cell permeable and have been used widely to label the Golgi, but they bleach too rapidly for prolonged imaging or super-resolution methods. Photostable dyes typically used for STED microscopy, such as commercially available ATTO® 647N and STAR635, suffer respectively from non-specific 1779117.1 binding and lack of cell permeability, and are ill suited for live cell STED microscopy of intracellular structures such as the Golgi.

There is a need in the art to identify novel compositions, and methods using same, that may be used for imaging intracellular structures. Such compositions should be cell permeable and allow for live cell microscopy of intracellular structures. The present invention addresses and meets this need.

BRIEF SUMMARY OF THE INVENTION

The invention provides a trans-cyclooctene-containing lipid, or a salt, solvate, stereoisomer, or any mixtures thereof, wherein the lipid comprises TCO-LINK-LIPID, wherein TCO is a trans-cyclooctene group, LINK is a bivalent linker, and LIPID is a lipid.

In certain embodiments, TCO is selected from the group consisting of:

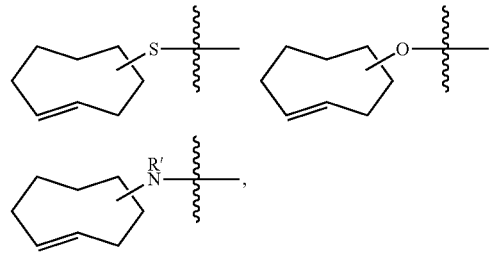

wherein R' is H or optionally substituted $C_1$-$C_6$ alkyl, and wherein the heteroatom is not attached to the ring double bond.

In certain embodiments, TCO is selected from the group consisting of:

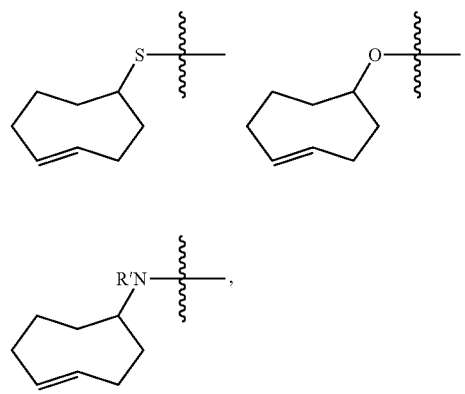

wherein R' is H or optionally substituted $C_1$-$C_6$ alkyl.

In certain embodiments, LIPID comprises at least one selected from the group consisting of a sphingolipid, phospholipid, sterol lipid and fatty acid. In other embodiments, LIPID comprises at least one selected from the group consisting of sphingosine, 1-phosphocholine-sphingosine, 1-phosphoethanolamine-sphingosine, and a 1-glycosyl-sphingosine. In yet other embodiments, LIPID comprises sphingosine. In yet other embodiments, LIPID comprises sphingosine and is covalently conjugated to LINK through the 2-amino group of sphingosine.

In certain embodiments, LINK comprises —X(CR'R")$_n$C(═O)—, wherein X is covalently conjugated to TCO and is selected from the group consisting of a covalent bond, —C(═O)—, —C(═O)O— and —C(═O)NR'—; each occurrence of R' and R" is independently selected from the group consisting of H and optionally substituted $C_1$-$C_6$ alkyl; and n is an integer ranging from 1 to 20. In other embodiments, n is 5.

In certain embodiments, the lipid is Cer-TCO or a salt, solvate, stereoisomer, or any mixtures thereof.

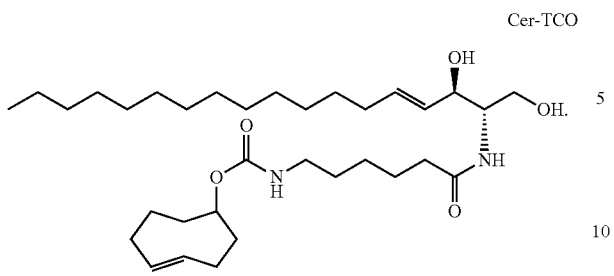

The invention further provides a tetrazine-containing dye, or a salt, solvate, stereoisomer, or any mixtures thereof, which is:

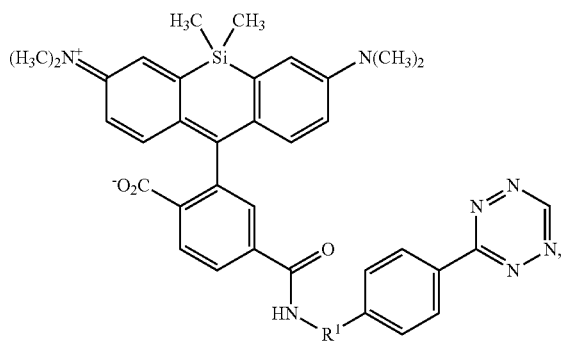

wherein $R^1$ is —$(CH_2)_n$— or —$(CH_2CH_2O)_n(CH_2)_m$—; n is an integer ranging from 1 to 6; and m is 0, 1 or 2. In certain embodiments, $R^1$ is —$(CH_2)$—.

In certain embodiments, the dye is SiR-Tz, or a salt, solvate, stereoisomer, or any mixtures thereof:

SiR-Tz

The invention further provides a compound, or a salt, solvate, stereoisomer, or any mixtures thereof, of formula:

(I)

wherein in (I): $R^1$ is —$(CH_2)_n$— or —$(CH_2CH_2O)_n(CH_2)_m$—; m is 0, 1 or 2; each occurrence of n is independently an integer ranging from 1 to 6; $R^2$ is S, O or NR'; LINK comprises —$X(CR'R'')_{1-20}C(=O)$—, wherein X is covalently conjugated to $R^2$ and is selected from the group consisting of a covalent bond, —$C(=O)$—, —$C(=O)O$— and —$C(=O)NR'$—; LIPID comprises a sphingolipid; and, each occurrence of R' and R'' is independently selected from the group consisting of H and optionally substituted $C_1$-$C_6$ alkyl.

In certain embodiments, in (I) $R^1$ is —$CH_2$—. In other embodiments, in (I) $R^2$ is S, O or NH. In yet other embodiments, in (I) LINK is —$X(CH_2)_{1-20}C(=O)$—. In yet other embodiments, in (I) LINK is —$C(=O)NH(CH_2)_5C(=O)$—. In yet other embodiments, (I) is a compound of formula (IA), or a salt, solvate, stereoisomer, or any mixtures thereof:

(IA)

In certain embodiments, the compound is Cer-SiR, or a salt, solvate, stereoisomer, or any mixtures thereof:

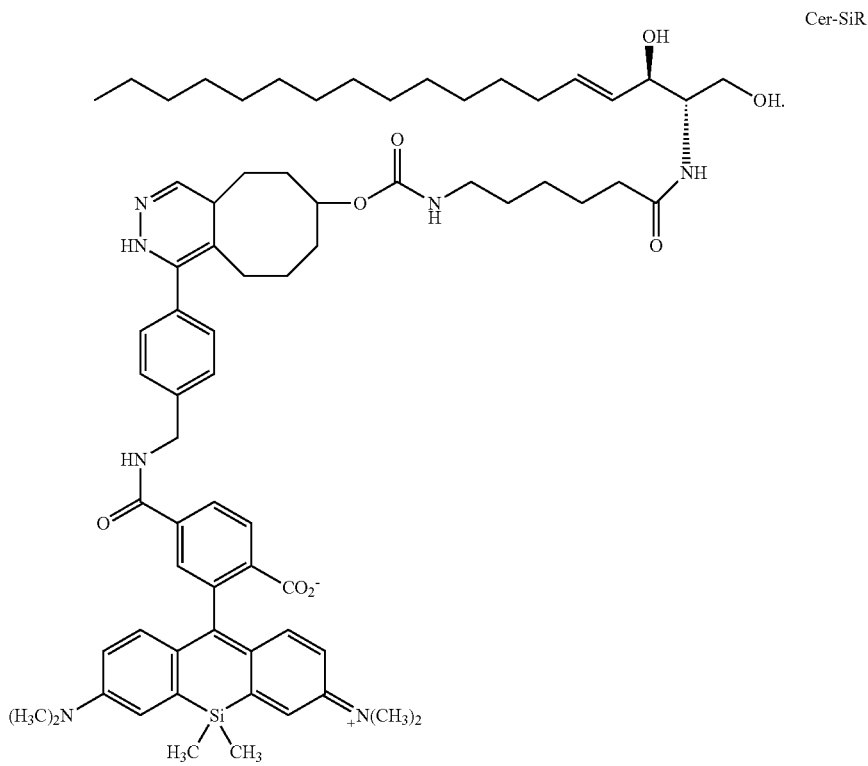

Cer-SiR

The invention further provides a method of labeling an intracellular structure in a cell. In certain embodiments, the method comprises contacting the cell with at least one trans-cyclooctene-containing lipid of the present invention, wherein the lipid associates with the intracellular structure in the cell. In other embodiments, the method comprises contacting the cell with at least one tetrazine-containing dye of the present invention, wherein the tetrazine-containing dye undergoes a cycloaddition reaction with the at least one trans-cyclooctene-containing lipid in the intracellular structure, whereby the cycloaddition product labels the intracellular structure.

In certain embodiments, the cell is in at least one state selected from the group consisting of in vitro, ex vivo and in vivo. In other embodiments, the intracellular structure is visualized using at least one method selected from the group consisting of 3D confocal microscopy, STED super-resolution microscopy, and single molecule switching (SMS) super-resolution imaging. In yet other embodiments, the cycloaddition product is photostable. In yet other embodiments, the intracellular structure comprises at least one selected from the group consisting of the Golgi and trans-Golgi network. In yet other embodiments, the tetrazine-containing dye, trans-cyclooctene-containing lipid and cycloaddition product do not have a significant effect on cell morphology. In yet other embodiments, the tetrazine-containing dye, trans-cyclooctene-containing lipid and cycloaddition product do not have a significant effect on mobility of a protein within the Golgi, or in cargo traffic from the ER through the Golgi and to the plasma membrane. In yet other embodiments, the tetrazine-containing dye is SirR-Tz, or a salt, solvate, stereoisomer, or any mixtures thereof. In yet other embodiments, the trans-cyclooctene-containing lipid is Cer-TCO, or a salt, solvate, stereoisomer, or any mixtures thereof. In yet other embodiments, the cycloaddition product is Cer-SiR, or a salt, solvate, stereoisomer, or any mixtures thereof. In yet other embodiments, the cell is human.

The invention further provides a kit comprising a tetrazine-containing dye, trans-cyclooctene-containing lipid, applicator, and instructional material for use thereof, wherein the instructional material comprises instructions for labeling an intracellular structure in a cell using the dye and the lipid.

In certain embodiments, the tetrazine-containing dye is SirR-Tz, or a salt, solvate, stereoisomer, or any mixtures thereof. In other embodiments, the trans-cyclooctene-containing lipid is Cer-TCO, or a salt, solvate, stereoisomer, or any mixtures thereof.

BRIEF DESCRIPTION OF THE DRAWINGS

The following detailed description of certain embodiments of the invention will be better understood when read in conjunction with the appended drawings. For the purpose of illustrating the invention, illustrated in the drawings are certain embodiments. It should be understood, however, that the invention is not limited to the precise arrangements and instrumentalities of the embodiments illustrated in the drawings.

FIGS. 2A-2D illustrate the finding that Cer-TCO localizes and reacts with SiR-Tz to visualize the Golgi in live cells. FIG. 2A: HeLa cells expressing the Golgi reporter protein GalNAcT2-GFP were treated with Cer-TCO, subjected to a temperature block to accumulate the ceramide lipid in the Golgi, and labeled with SiR-Tz. FIGS. 2B-2D: Incubation with SiR-Tz alone did not label the cells, whereas treatment with Cer-TCO and Sir-Tz led to a reaction product (red) that colocalizes with the Golgi marker GalNAcT2-GFP (green).

FIG. 3A: Endpoint trafficking assay using TfRc-$F_M$4-pH and "DID" solubilizer to distinguish between cargo that reached the plasma membrane or remained inside the cell. FIG. 3B: HeLa cells expressing TfRc-$F_M$4-pH (green) were treated with or without Cer-TCO and SiR-Tz and fixed 0 or 60 min after the "D/D" solubilizer-promoted release of TfRc-$F_M$4-pH from the ER. Cells were immunostained to visualize the Golgi (magenta) and TfRc-$F_M$4-pH on the cell surface (red). At 0 min, TfRc-$F_M$4-pH (green) was localized to the ER, whereas at 60 min it was localized to the cell surface. Nuclei were stained with Hoechst 33342 (blue). FIG. 3C: Ratio of red/green channels shows the fraction of cargo (TfRc-$F_M$4-pH) that reached the surface.

FIG. 4A: Cells expressing GalNAcT2-GFP (green) were labeled with Cer-TCO and SiR-Tz, photobleached, and the fluorescence recovery after photobleaching (FRAP) monitored vs. time. FIG. 4B: Representative examples of fluorescence recovery at 0-490 sec after photobleaching cells treated with or without Cer-TCO/SiR-Tz. FIG. 4C: Plots showing that fluorescence recovery occurred at a similar rate and extent irrespective of Cer-TCO/SiR-Tz concentration and with or without temperature block. FIG. 4D: Differential effects of prolonged illumination on GalNacT4-GFP (green) cells labeled with BODIPY-Cer (green) or Cer-TCO and SiR-Tz (red). D=cells dividing; *=dying cell. FIG. 4E: Quantification of live cell data from FIG. 4D shows the relative number of healthy cells as a function of time after different conditions.

FIG. 5A: Images show cells labeled with the lipid Cer-SiR (Cer-TCO+SiR-Tz), BODIPY-Cer, or the protein Rab6-SNAP labeled with SiR (Rab6-SNAP+SiR-BG) after acquisition of 1-120 3D image stacks (21 images/stack). FIG. 5B: Plot of the relative intensity of cells labeled with different lipid and protein probes as a function of the number of acquired 3D stacks.

FIG. 6A: Confocal and STED images of the Golgi in live cells treated with Cer-TCO and SiR-Tz. Line traces through the Golgi (yellow) show the greatly improved resolving power of STED (right panel). FIG. 6B: Kymographs (line profile vs. time) of fixed cells imaged by STED in which the Golgi was labeled with Cer-SiR or SiR-SNAP-Rab6 (a Golgi targeted protein); the signal decayed much more quickly when the protein was labeled with SiR. FIG. 6C: Time lapse STED of vesicle budding and trafficking out of the Golgi (green arrowhead).

FIG. 15 is a set of panels illustrating that incubation with solutions of preassembled Cer-SiR did not lead to Golgi labeling. Without wishing to be limited by any theory, the poorly observed signal of SiR could be due to low cell permeability of Cer-SiR.

DETAILED DESCRIPTION OF THE INVENTION

Figure 1:
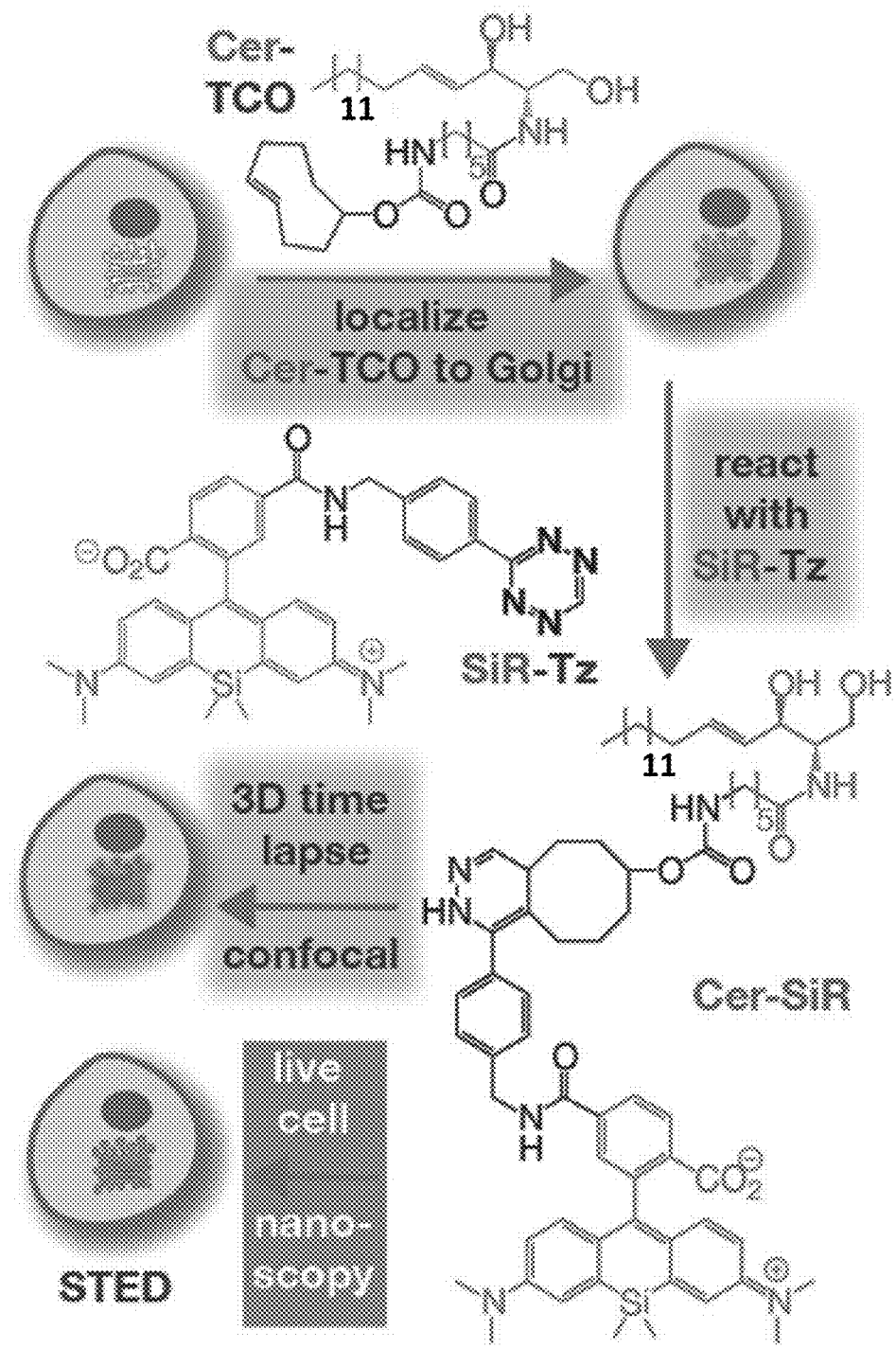
FIG. 1 is a schematic illustration of the two-step procedure for high-density labeling of the Golgi in living cells. Cells are treated first with Cer-TCO, a trans-cyclooctene-containing ceramide lipid, and then reacted with SiR-Tz, a tetrazine derivative of a highly photostable silicon-containing rhodamine dye. The product of this reaction, Cer-SiR (a single isomer thereof being depicted herein) allows extensive live cell imaging by 3D confocal and STED super-resolution microscopy.

The invention relates in part to the unexpected discovery of novel compositions that can be used to visualize Golgi structure and dynamics at super-resolution in a live cell. In certain embodiments, the compositions of the invention allow for the visualization of lipid bodies in the cell.

In certain embodiments, the invention provides a trans-cyclooctene-containing lipid. In other embodiments, the invention provides a tetrazine-containing near-IR dye. In yet other embodiments, the trans-cyclooctene-containing lipid and the tetrazine-containing near-IR dye react through the "tetrazine-click" reaction to generate a highly photostable dye that enables prolonged live cell imaging of the Golgi apparatus, such as, but not limited to, 3D confocal and/or STED microscopies.

In certain embodiments, the dyes of the invention are non-toxic at concentrations required for live cell imaging. In other embodiments, the dyes of the invention are non-toxic at concentrations of at least 100 nM, or at least 250 nM, or at least 500 nM, or at least 750 nM, or at least 1 μM, or at least at 2 μM, or at least at 5 μM, or at least at 10 μM, or at concentrations higher than 10 μM. In yet other embodiments, the dyes of the invention do not perturb the mobility of Golgi-resident enzymes or the traffic of cargo from the endoplasmic reticulum through the Golgi and to the plasma membrane. In yet other embodiments, the dyes of the invention are more photostable than commercially available lipid dyes.

The invention should not be construed to be limited to the trans-cyclooctene-containing lipids, the tetrazine-containing near-IR dyes or cycloaddition products disclosed herein. In certain embodiments, the compositions of the invention include other trans-cyclooctene-containing lipids, tetrazine-containing near-IR dyes and/or cycloadditon dyes that can be used to visualize Golgi structure and dynamics at super-resolution in a live cell. Such compositions may be prepared using the methods and techniques described herein, and used within the methods of the invention.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, specific methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, the term "abnormal" when used in the context of organisms, tissues, cells or components thereof, refers to those organisms, tissues, cells or components thereof that differ in at least one observable or detectable characteristic (e.g., age, treatment, or time of day) from those organisms, tissues, cells or components thereof that display the "normal" (expected) respective characteristic. Characteristics that are normal or expected for one cell or tissue type might be abnormal for a different cell or tissue type.

"About" as used herein when referring to a measurable value such as an amount, a temporal duration, and the like, is meant to encompass variations of specifically ±20%, specifically ±10%, specifically ±5%, specifically ±1%, or specifically ±0.1% from the specified value, as such variations are appropriate to perform the disclosed methods.

hexyl, and cyclopropylmethyl. Most preferred is $(C_1-C_6)$ alkyl, such as, but not limited to, ethyl, methyl, isopropyl, isobutyl, n-pentyl, n-hexyl and cyclopropylmethyl.

As used herein, the term "Cer-TCO" refers to (E)-cyclooct-4-en-1-yl (6-(((2S,3R,E)-1,3-dihydroxyoctadec-4-en-2-yl)amino)-6-oxohexyl)carbamate, or a salt, solvate, stereoisomer, or any mixtures thereof:

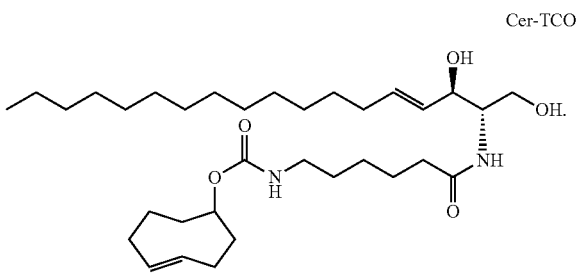 [SMILES: CCCCCCCCCCCCC/C=C/[C@@H](O)[C@H](CO)NC(=O)CCCCCNC(=O)OC1CC/C=C/CCC1]

Cer-TCO

As used herein, the term "Cer-SiR" refers to 4-((4-(7-(((6-(((2S,3R,E)-1,3-dihydroxyoctadec-4-en-2-yl)amino)-6-oxohexyl)carbamoyl)oxy)-2,4a,5,6,7,8,9,10-octahydrocyclooocta[d]pyridazin-1-yl)benzyl)carbamoyl)-2-(7-(dimethylamino)-3-(dimethyliminio)-5,5-dimethyl-3,5-dihydrodibenzo[b,e]silin-10-yl)benzoate, or a salt, solvate, stereoisomer, or any mixtures thereof:

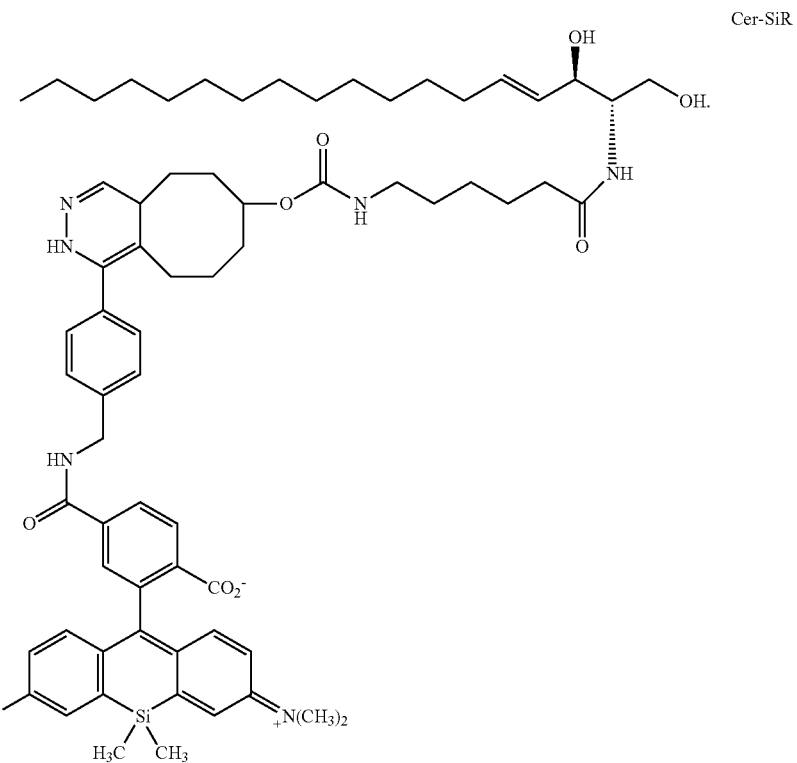

Cer-SiR

As used herein, the term "alkyl" by itself or as part of another substituent means, unless otherwise stated, a straight or branched chain hydrocarbon having the number of carbon atoms designated (i.e., $C_1-C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, As used herein, the term "composition" refers to a mixture of at least one compound useful within the invention with an acceptable liquid (which may be a solvent) or solid. The composition may facilitate manipulation of the compound, transfer of the compound, or use of the compound within the methods of the invention, in non-limiting examples.

As used herein, a "disease" is a state of health of an animal wherein the animal cannot maintain homeostasis, and wherein if the disease is not ameliorated then the animal's health continues to deteriorate.

As used herein, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "GFP" refers to green fluorescent protein.

As used herein, the term "Golgi" refers to the Golgi apparatus, Golgi complex, Golgi body, or simply the Golgi.

"Instructional material" as that term is used herein includes a publication, a recording, a diagram, or any other medium of expression that can be used to communicate the usefulness of the composition and/or method of the invention in a kit. The instructional material of the kit may, for example, be affixed to a container that contains the compound and/or composition of the invention or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

As used herein, the terms "patient," "subject," "individual" and the like are used interchangeably, and refer to any animal, or organs, tissues or cells thereof whether in vitro or in situ, amenable to the methods described herein. In certain embodiments, the patient, subject or individual is a vertebrate. In other embodiments, the patient, subject or individual is a mammal. In yet other embodiments, the patient, subject or individual is a human.

As used herein, the term "RT" or "rt" refers to room temperature.

As used herein, the term "SiR-Tz" refers to 4-((4-(1,2,4,5-tetrazin-3-yl)benzyl)carbamoyl)-2-(7-(dimethylamino)-3-(dimethyliminio)-5,5-dimethyl-3,5-dihydrodibenzo[b,e]silin-10-yl)benzoate, or a salt, solvate, stereoisomer, or any mixtures thereof:

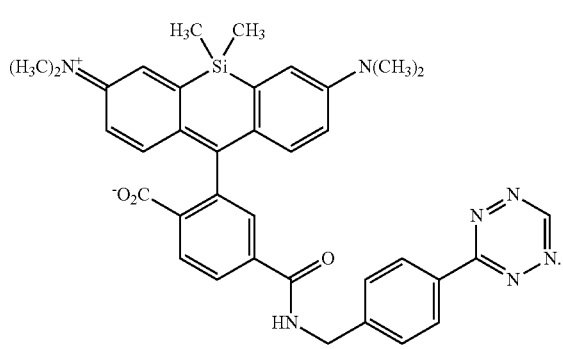

SiR-Tz

As used herein, the term "sphingosine" refers to 2-amino-4-octadecene-1,3-diol, or a salt, solvate, stereoisomer, or any mixtures thereof.

As used herein, the term "STED" refers to stimulated emission depletion microscopy.

As used herein, the term "substituted" means that an atom or group of atoms has replaced hydrogen as the substituent attached to another group.

As used herein, the term "substituted alkyl" means alkyl substituted by one, two or three substituents selected from the group consisting of halogen, —OH, alkoxy, tetrahydro-2-H-pyranyl, —NH$_2$, —N(CH$_3$)$_2$, (1-methyl-imidazol-2-yl), pyridin-2-yl, pyridin-3-yl, pyridin-4-yl, —C(═O)OH, trifluoromethyl, —C≡N, —C(═O)O(C$_1$-C$_4$)alkyl, —C(═O)NH$_2$, —C(═O)NH(C$_1$-C$_4$)alkyl, —C(═O)N((C$_1$-C$_4$)alkyl)$_2$, —SO$_2$NH$_2$, —C(═NH)NH$_2$, and —NO$_2$; in certain embodiment containing one or two substituents selected from halogen, —OH, alkoxy, —NH$_2$, trifluoromethyl, —N(CH$_3$)$_2$, and —C(═O)OH; in another embodiment selected from halogen, alkoxy and —OH. Examples of substituted alkyls include, but are not limited to, 2,2-difluoropropyl, 2-carboxycyclopentyl and 3-chloropropyl.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.1, 5.3, 5.5, and 6. This applies regardless of the breadth of the range.

DISCLOSURE

As described herein, the invention provides a strategy to visualize Golgi structure and dynamics at super-resolution in a live cell using a novel lipid-based fluorescent probe as contrast agent.

In certain non-limiting embodiments, the invention provides a trans-cyclooctene-containing ceramide lipid (Cer-TCO) and a highly reactive, tetrazine-tagged, near-IR dye (SiR-Tz). These reagents assemble via an extremely rapid "tetrazine-click" reaction into Cer-SiR, a "vital dye" that requires no transfection and whose extreme photostability enables prolonged live cell imaging by 3D confocal and/or STED microscopies (FIG. 1). Cer-SiR is non-toxic at concentrations as high as 2 μM and does not perturb either the mobility of enzymes within the Golgi or the traffic of cargo from the endoplasmic reticulum through the Golgi and to the plasma membrane.

To evaluate whether the Golgi could be selectively imaged using Cer-SiR, HeLa cells that stably expressed a protein fusion composed of GFP and N-acetyl-galactosaminyltransferase 2 (GalNAcT2), a transmembrane protein that localizes to the Golgi with high specificity (Storrie, et al., 1998, J. Cell Biol. 143:1505-1521), were used. These cells were treated with 2 μM Cer-TCO (5 min), maintained at 19.5° C. for 60 min to localize the lipid to the Golgi, treated subsequently with 2 μM SiR-Tz (30 min), and visualized using confocal microscopy (FIG. 2A).

Figure 9:
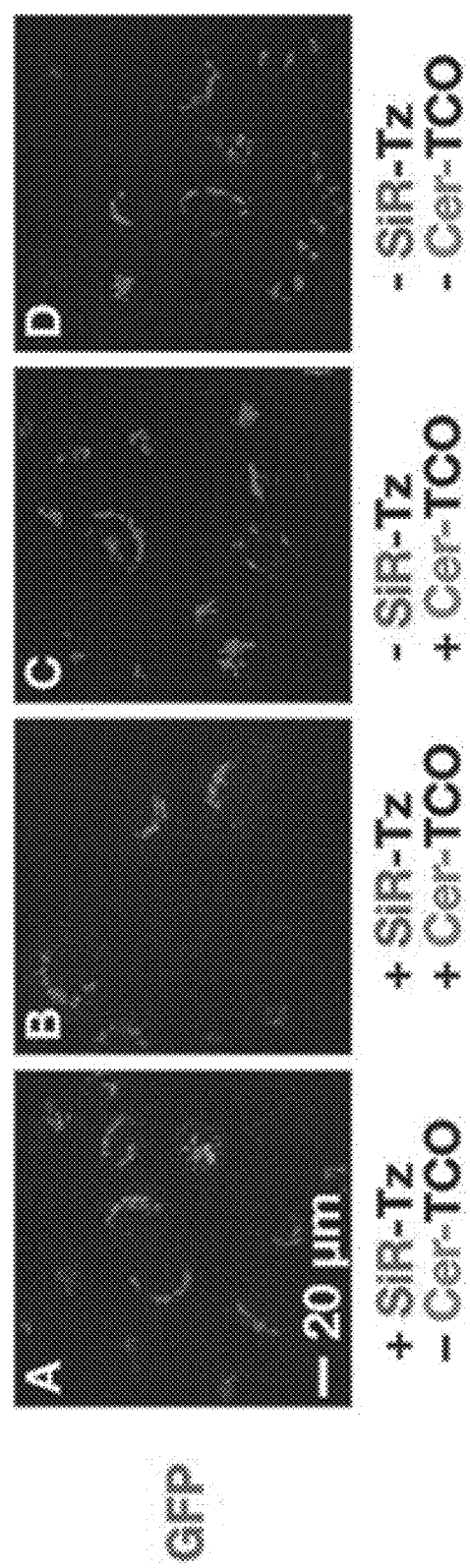
FIG. 9, comprising Panels A-D, illustrates the finding that the Golgi marker protein GalNAcT2-GFP localized to the Golgi in a manner that was independent of the presence or absence of SiR-Tz and/or Cer-TCO.

As expected, GalNAcT2-GFP displayed a typical Golgi perinuclear crescent localization regardless of whether or not Cer-TCO or SiR-Tz were added (FIGS. 2B & 9). However, treatment of cells with Cer-TCO followed by SiR-Tz led to bright red labeling at the Golgi region (FIGS.

Figure 10:
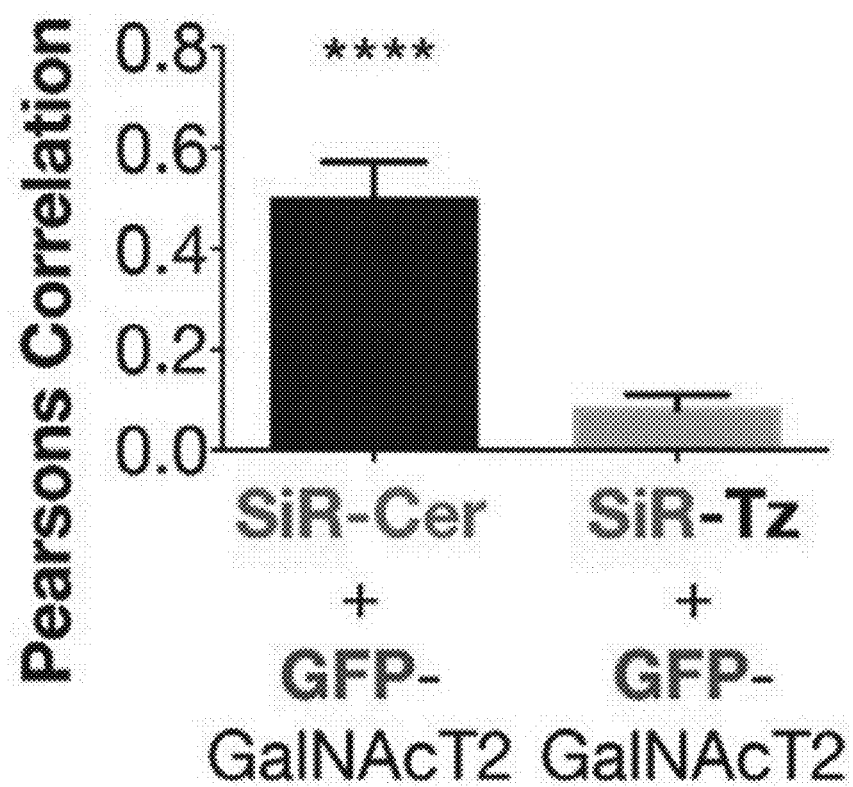
FIG. 10 is a bar graph illustrating the Pearson correlation between SiR-Cer and GalNAcT2-GFP and SiR-Tz and GalNAcT2-GFP, respectively.

2C-2D). Premixed Sir-Tz and Cer-TCO are not suitable for Golgi labeling, presumably due to the low cell permeability. The GalNAcT2-GFP and Cer-SiR signals colocalized with a Pearson's coefficient of 0.50±0.02; the corresponding value for the signals from GalNAcT2-GFP and SiR-Tz was 0.08±0.01 (p<0.0001) (FIG. 10), supporting that Cer-TCO effectively localized to the Golgi and reacted efficiently with SiR-Tz.

Figure 3A:
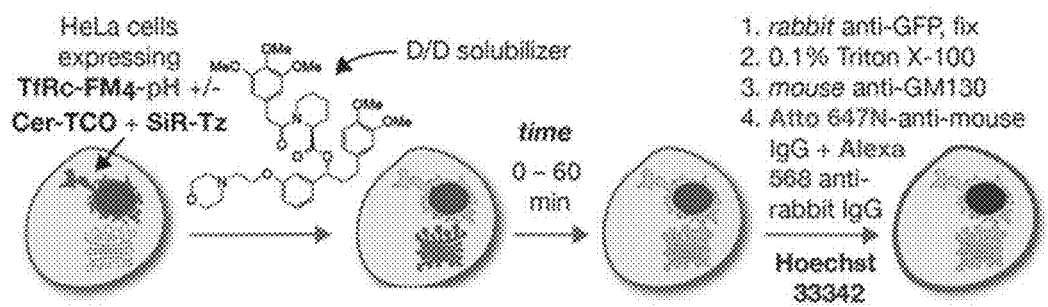
FIGS. 3A-3C illustrate intracellular localization of compositions of the invention.
Figure 3B:
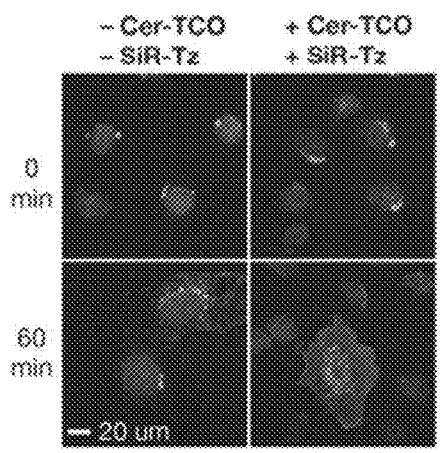

To verify that the Golgi apparatus retained its function in cells treated with Cer-TCO and SiR-Tz, traffic both through and within the Golgi was monitored. First, HeLa cells that transiently expressed the fusion protein TfRc-$F_M$4-pH (which comprises the transferrin receptor (TfRc), four F36M-FKBP ($F_M$) domains, and pHluorin, a pH sensitive mutant of GFP) were used. Fusion proteins containing four $F_M$ domains aggregate and remain trapped in the endoplasmic reticulum, but de-aggregate rapidly upon addition of "D/D"-solubilizer, a rapamycin fragment analog (Clackson, et al., 1998, Proc. Natl. Acad. Sci. U.S.A. 95:10437-10442; Clontech #635054) (FIG. 3A). Expression of TfRc-$F_M$4-pH in HeLa cells led to high levels of GFP fluorescence in large perinuclear aggregates in the endoplasmic reticulum (FIG. 3B, 0 min, left panel). Addition of "DID" solubilizer caused the TfRc-$F_M$4-pH to traffic to the Golgi apparatus and subsequently to the plasma membrane, where it was detected on the cell surface by immunostaining with an Alexa-568 tagged anti-GFP antibody (FIG. 3B, 60 min, left panel). Addition of Cer-TCO and SiR-Tz (as described elsewhere herein) caused no obvious change in the ability of TfRc-$F_M$4-pH to traffic through the Golgi and to the plasma membrane (FIG. 3B, 60 min, right panel).

Figure 3C:
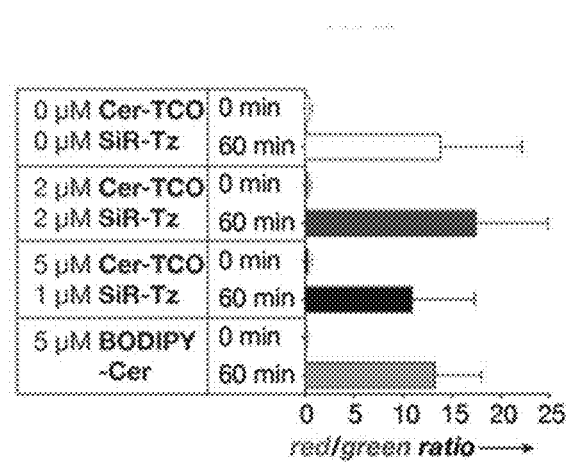
Figure 11:
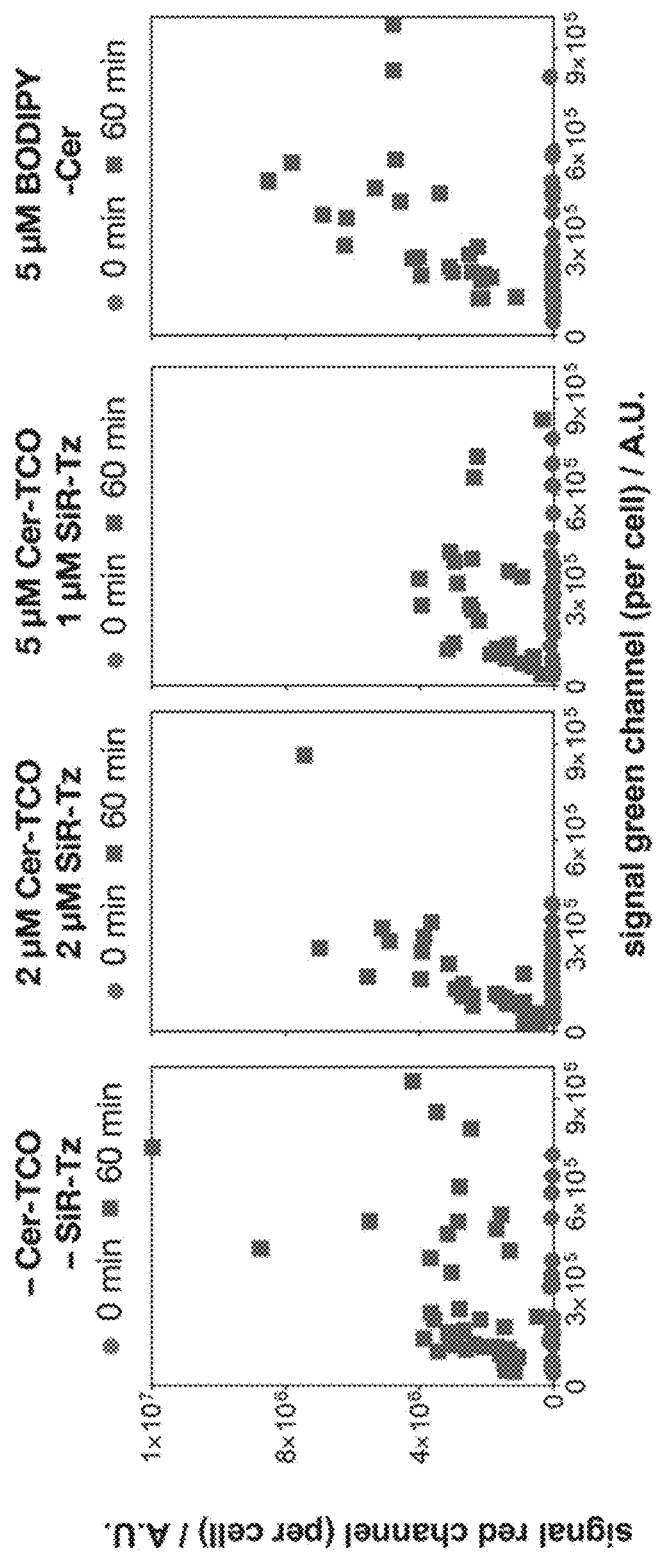
FIG. 11 is a set of graphs illustrating red and green signal of individual cells under various conditions.
Figures 12A, 12B, 13:
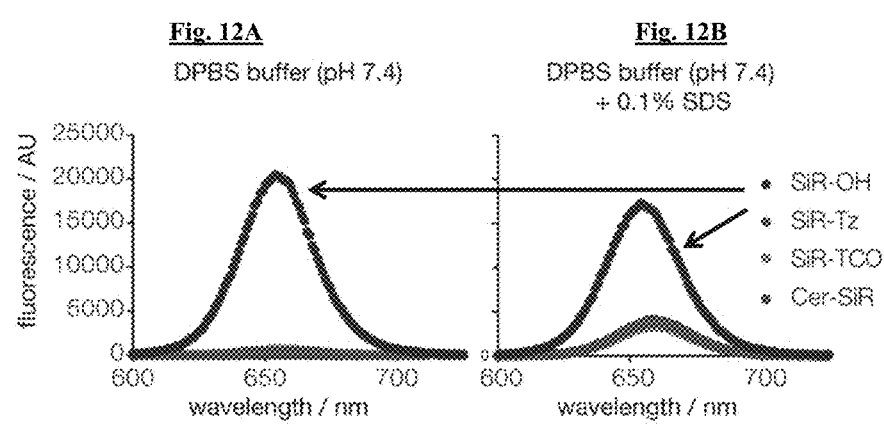
FIGS. 12A-12B illustrate emission spectra (excitation at 610 nm) of solutions of 1 μM SiR—OH (•), 1 μM SiR-Tz (•), 1 μM SiR-Tz+10 μM TCO-OH (•) and 1 μM SiR-Tz+10 μM Cer-TCO (•) in (FIG. 12A) DPBS pH 7.4 and (FIG. 12B) DPBS pH 7.4 supplemented with 0.1% SDS, respectively. The arrows indicate the curves for SiR—OH; all other curves correspond to the lower curves.
FIG. 13 is table illustrating photophysical properties of SiR—OH, SiR-Tz, SiR-TCO and Cer-SiR in DPBS pH 7.4 with or without 0.1% SDS. nd=not determined due to low absorption of 1 μM solutions. A value of 100 was randomly assigned to the relative fluorescence ($F_{rel}$) of SiR—OH.
Figure 14:
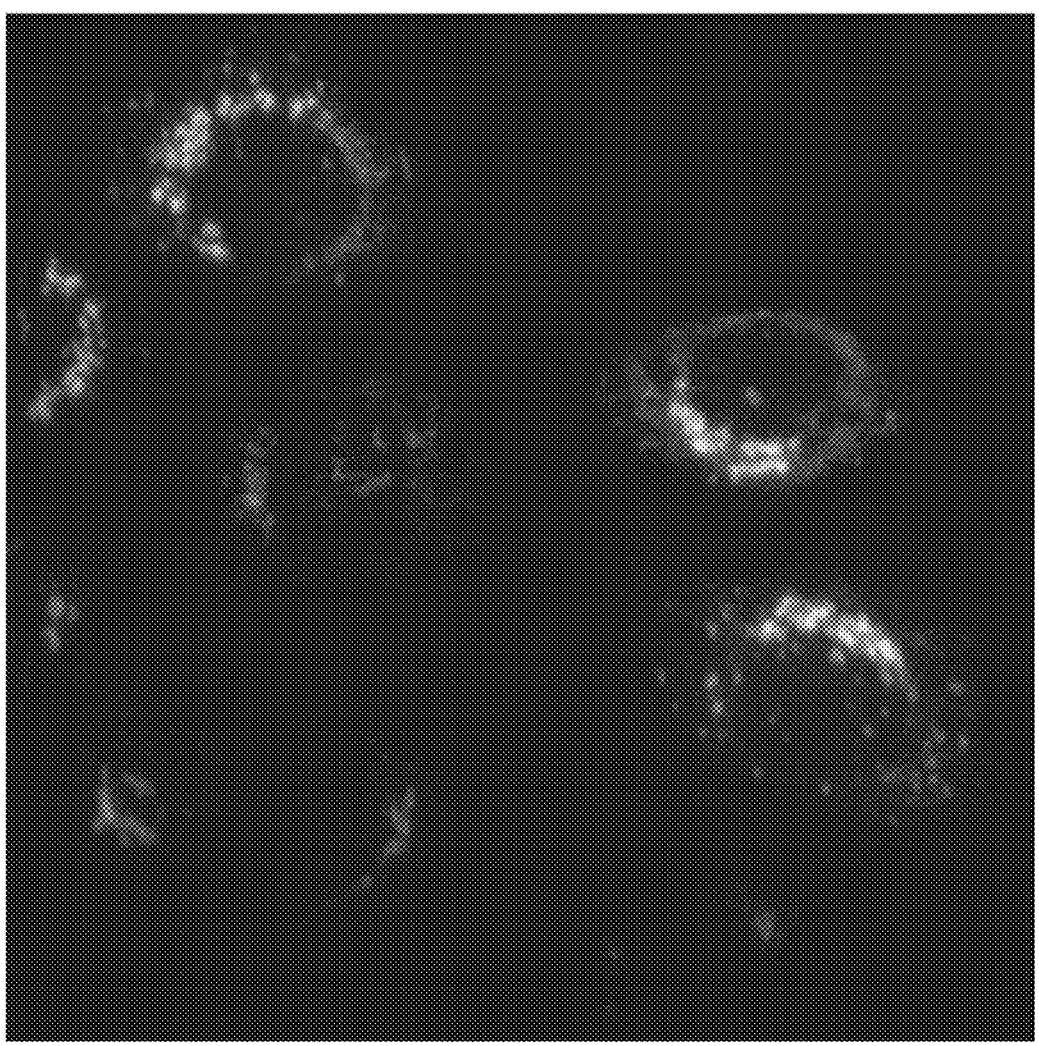
FIG. 14 is an image illustrating an enlarged version of the lower panel in FIG. 2D (2 μM SiR-Tz+2 μM Cer-TCO).

To quantitatively determine if various concentrations of Cer-TCO/SiR-Tz perturbed traffic of TfRc-$F_M$4-pH through the Golgi, this assay was adapted to ratiometrically monitor the fraction of TfRc-$F_M$4-pH that reached the plasma membrane in multiple cells in the presence or absence of Cer-TCO/SiR-Tz. Specifically, the total fluorescence due to TfRc-$F_M$4-pH (green channel) in multiple single cells was compared to the amount on the cell surface by detecting the latter with an Alexa-568 anti-GFP antibody (red channel) at 0 and 60 min after the addition of "DID" solubilizer. The assay was controlled internally as it monitored the fractional localization of a single protein (TfRc-$F_M$4-pH) in two channels, as opposed to monitoring two different proteins whose co-expression levels can vary. Cells were treated with 0, 2 or 5 µM of Cer-TCO and SiR-Tz and the amount of TfRc-$F_M$4-pH within the cell and at the plasma membrane was quantified by integrating the green and red signal of cells with ImageJ at 0 min (immediately after addition of "DID" solubilizer) and after 60 min (FIG. 3C). Excluding highly overexpressing cells, plots of the raw GFP (green) and Alexa-568 (red) signals (FIG. 11) or the red/green ratio (FIG. 3C) were nearly identical, regardless of whether the cells were treated with Cer-TCO and SiR-Tz or not. This ratiometric inside/out assay provides evidence that Cer-TCO and SiR-Tz had no effect on the fraction of TfRc-$F_M$4-pH that trafficked from the ER to plasma membrane via the Golgi apparatus.

Figure 4A:
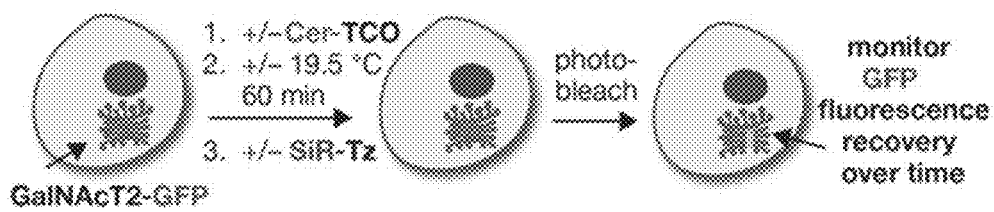
FIGS. 4A-4E illustrate the finding that intra-Golgi trafficking is unaffected by Cer-TCO and SiR-Tz.
Figure 4B:
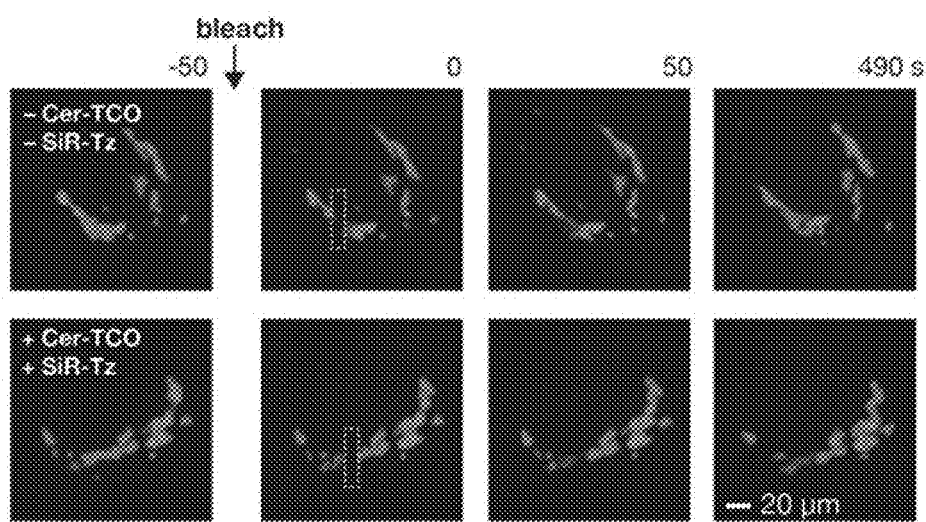
Figure 4C:
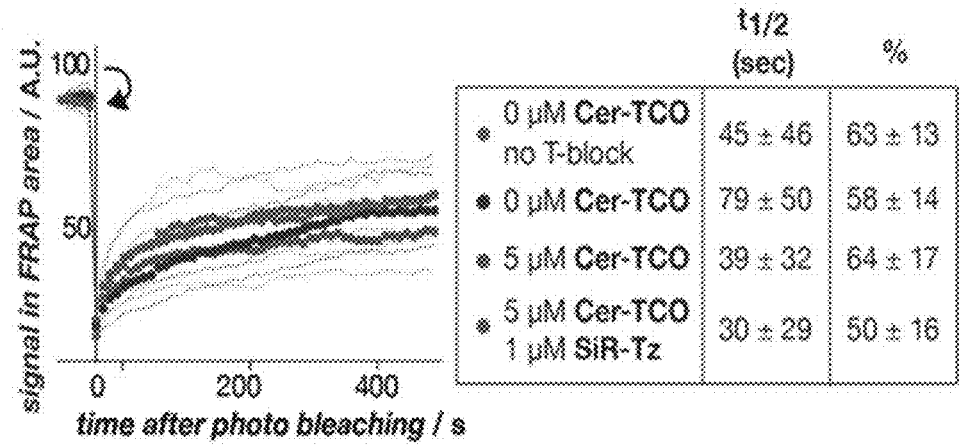

To further test whether the combination of Cer-TCO and SiRTz affected traffic within the Golgi, HeLa cells that stably expressed the GFP-tagged transmembrane Golgi enzyme GalNAcT2 (Storrie, et al., 1998, J. Cell Biol. 143:1505-1521) were used and its intra-organelle mobility was monitored using fluorescence recovery after photobleaching (FRAP) experiments (FIG. 4A). A small rectangular area of the Golgi (about 2.2 microns wide) was photobleached at 488 nm and the fluorescence recovery was monitored over 490 seconds (FIG. 4B). Both the $t_{1/2}$ of recovery and mobile fraction were unchanged when the cells were treated with Cer-TCO alone or the combination of 5 µM Cer-TCO and 1 µM SiR-Tz (FIG. 4C). Thus, treatment of cells with Cer-TCO alone or Cer-TCO and SiR-Tz led to no detectable change in the diffusion of GalNAcT2-GFP within the Golgi apparatus.

Figure 4D:
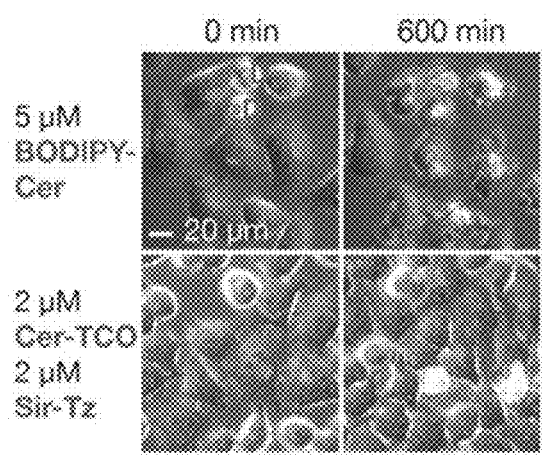
Figure 4E:
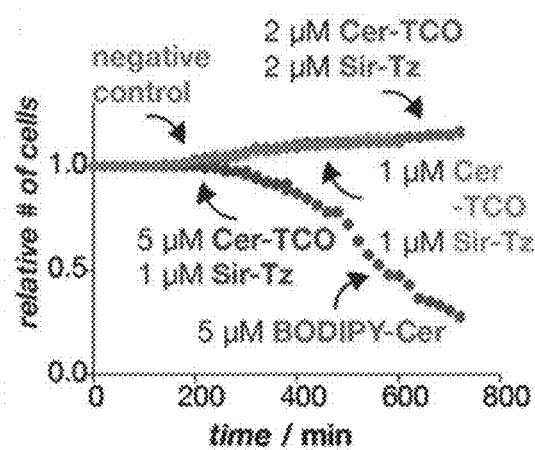

In the experiments described above, the cells were exposed to Cer-TCO/SiR-Tz for minutes, a relatively short time period. To evaluate whether this Golgi labeling strategy would result in cell- or photo-toxicity over prolonged periods (such as hours), HeLa cells were treated with varying concentrations of either Cer-TCO/SiR-Tz or BODIPY® FL C5-ceramide (BODIPY-Cer) (Marks, et al., 2008, Cell Biol. 130:819-832; Pagano, et al., 1991, J. Cell Biol. 113:1267-1279), a commercially available fluorescent dye that labels the Golgi. Live cell phase contrast and fluorescent images acquired every 10 min over a period of 6-10 hours revealed no adverse effect of 2 µM Cer-TCO/Sir-Tz on cell morphology or number (FIGS. 4D-4E). In contrast, 5 µM BODIPY-Cer (the concentration typically used in such studies; Marks, et al., 2008, Cell Biol. 130:819-832; Pagano, et al., 1991, J. Cell Biol. 113:1267-1279) induced cell rounding and de-attachment after about 6 hours (FIG. 4D). This observation indicates that caution must be present in using BODIPY-Cer in long-term experiments.

Taken together, the results of these three different assays indicate that neither the reaction components Cer-TCO and SiR-Tz nor their reaction product Cer-SiR has any significant effect on cell morphology (FIG. 4D), mobility of proteins (GalNAcT2-GFP) within the Golgi (FIG. 4A-4C), or in cargo traffic (TfRc-$F_M$4-pH) from the ER through the Golgi and to the plasma membrane (FIG. 3).

Figure 5A:
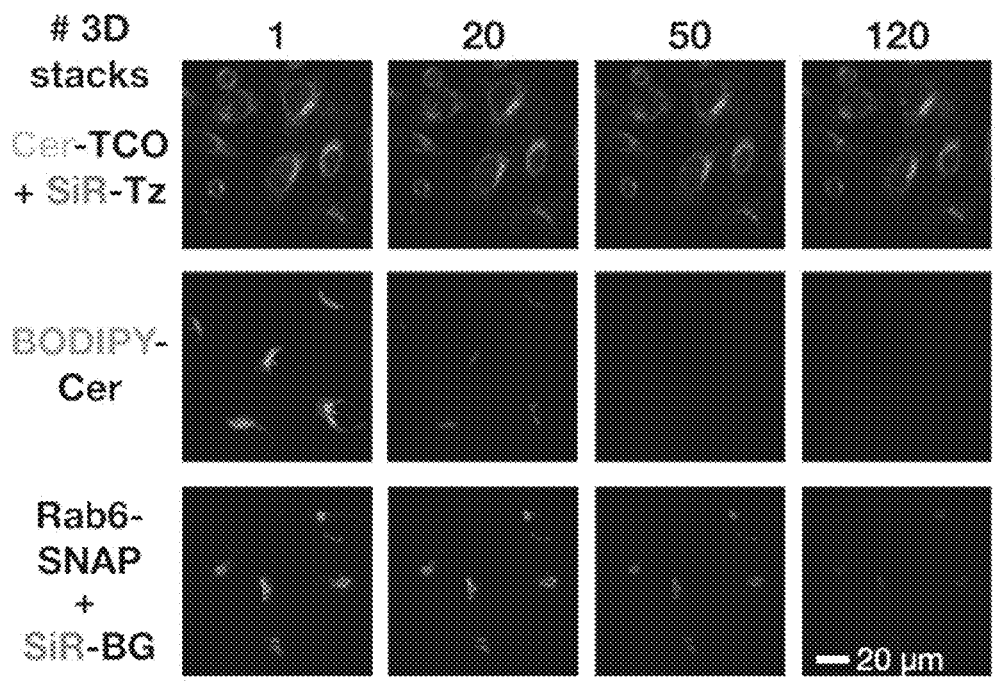
FIGS. 5A-5B illustrate the finding that Cer-SiR-labeled Golgi was extremely stable to spinning disk confocal imaging with prolonged illumination.
Figure 5B:
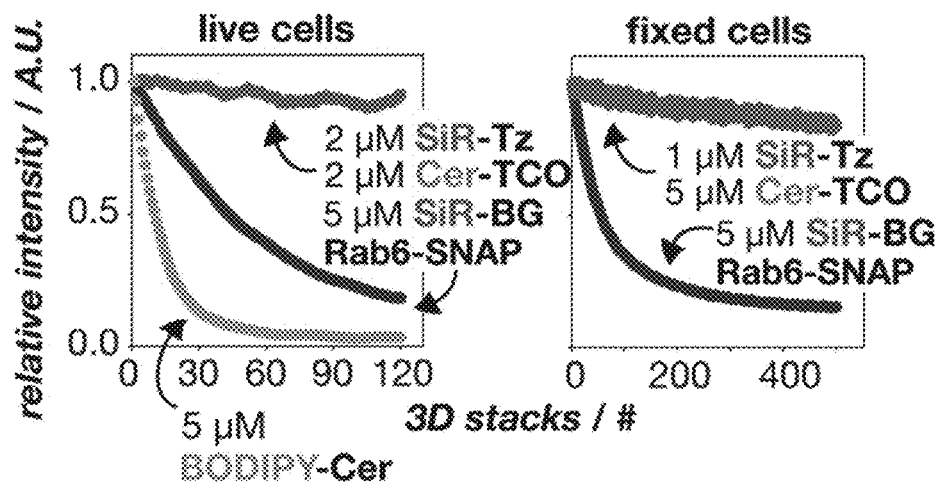

The relative photostability of Cer-TCO/SiR-Tz to both BODIPY-Cer and the SiR labeled SNAP-tag Golgi protein Rab6 was compared. The latter is the product of reaction between Rab6-SNAP and a benzyl guanine derivative of SiR (SiR-BG) (Lukinavicius, et al., 2013, Nature Chem. 5:132-139) and thus contains the same near-IR dye as SiR-Tz (FIGS. 5A-5B). HeLa cells were treated with Cer-TCO/SiR-Tz or BODIPY-Cer, while Rab6-SNAP-expressing cells were treated with SiR-BG. The cells were then examined in sequential 3D images using spinning disk confocal microscopy; 3D visualization limited fluorescence fluctuations due to axial sample drift. In each case, 3D "stacks" of 22 optical sections were acquired in series up to 500 times in live or fixed cells (FIGS. 5A-5B). In live cells, even under optimal imaging conditions the BODIPY-Cer fluorescent signal decreased by 50% after fewer than 15 stacks. In striking contrast, the fluorescent signal of cells treated with 2 µM Cer-TCO followed by 2 µM SiR-Tz decreased by only 10% after more than 120 3D stacks had been acquired. Consistent with a lower density of Rab6-SNAP protein in the Golgi, the signal from Rab6-SNAP-SiR decayed at an intermediate rate, decreasing by 50% after about 50 3D stacks. Even more striking differences between Rab6-SNAP-SiR and Cer-SiR were observed in fixed cells. After 500 3D stacks the fluorescent signal of Cer-SiR decreased 16% whereas that of Rab6-SNAP-SiR decreased by 84%. The initial intensity of Cer-SiR and Rab6-SNAP-SiR were similar in live and fixed cells, yet Cer-SiR was much more resistant to photobleaching. The net effect of the enhanced photostability of Cer-SiR is a vital dye that allows very long 3D time lapse imaging of Golgi dynamics.

The extreme photostability of Cer-SiR documented herein makes it well suited for STED microscopy, which uses confocal line scanning with a powerful donut-shaped depletion beam to achieve super-resolution. While in principle most fluorescent dyes are suitable for STED, the high intensity laser used to rapidly and repeatedly cycle molecules between their ground ($S_0$) and exited ($S_1$) states can drive dyes into triplet or other high energy states (e.g. $S_2$) and cause them to quickly bleach. While "anti-fade" triplet state quenchers such as Trolox and cyclooctatetraene can mitigate this effect, they are toxic to live cells. SiR is a remarkable dye for live cell STED, as it is cell permeable and similar in photostability to top STED dyes such as Atto 647N.

Figure 6A:
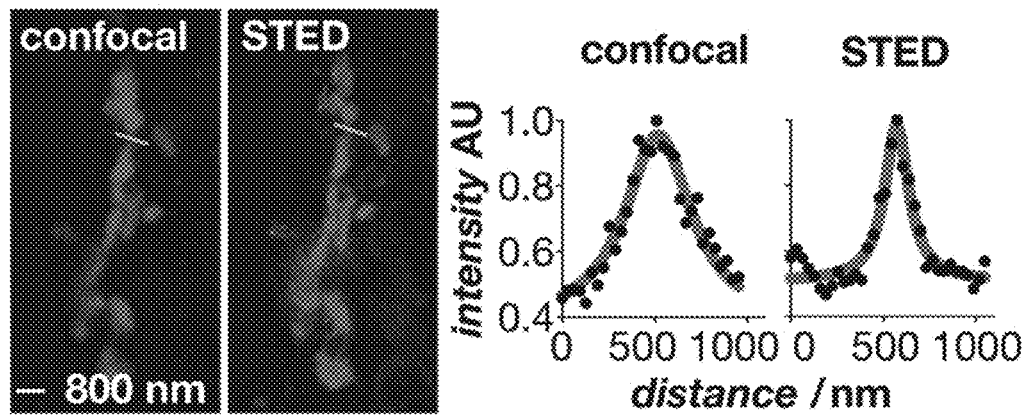
FIGS. 6A-6C illustrate super-resolution imaging of the Golgi in live cells using Cer-SiR.
Figure 6B:
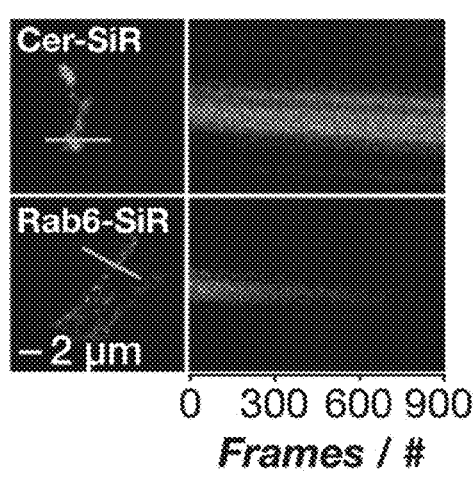
Figure 6C:
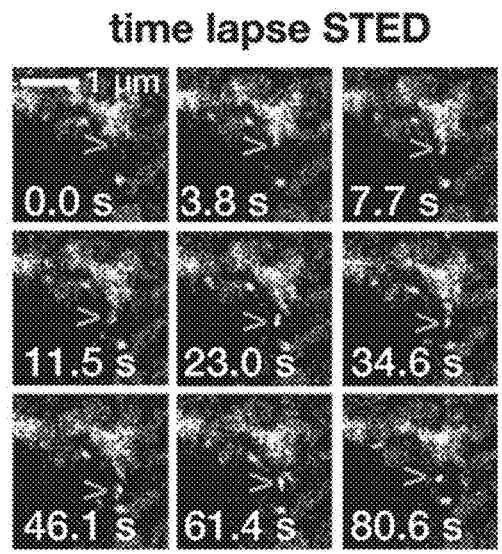

To evaluate the merits of Cer-SiR for super-resolution imaging of the Golgi, HeLa cells that stably expressed GalNAcT2-GFP were labeled with Cer-TCO and SiR-Tz, and imaged by confocal and STED microscopy using a commercial Leica instrument (FIGS. 6A-6C). The confocal and STED images were compared in FIG. 6A. The STED image was sharper, as seen in the image and the line profiles across the Golgi, demonstrating the suitability of Cer-SiR for STED microscopy. A direct comparison of the relative photostabilities of Cer-SiR and SiR-SNAP-Rab6 in fixed cells was performed using a custom STED microscope that is optimized for rapid image acquisition (FIG. 6B). Cells labeled with Cer-SiR or SiR-SNAPRab6 were continuously imaged at a rate of 0.52 frames/sec for 29 min (900 images) and the intensity of a line across the Golgi was plotted (FIG. 6B). The images of cells labeled with Cer-SiR were stable throughout all 900 images, whereas those labeled with SiRSNAP-Rab6 lost half their fluorescence after about 300 images; these data are consistent with the 3D spinning disk confocal results (FIGS. 5A-5B). Indeed, the exceptional resolution and photostability enabled by Cer-SiR allowed vesicles to be visualized budding and exiting the Golgi (FIG. 6C).

As demonstrated herein, the invention provides reagents that enable Golgi structure and dynamics to be visualized at super-resolution in live cells: a trans-cyclooctene-containing ceramide lipid (Cer-TCO) and a highly reactive, tetrazine-tagged near-IR dye assemble via an extremely rapid "tetrazine-click" reaction into Cer-SiR, a "vital dye" that enables prolonged live cell imaging of the Golgi apparatus by 3D confocal and STED microscopy. Cer-SiR is exceptionally photostable and greatly facilitates studies of Golgi dynamics in primary cells and tissue.

Compositions

The invention provides a trans-cyclooctene-containing lipid, or a salt, solvate, stereoisomer, or any mixtures thereof. In certain embodiments, the trans-cyclooctene-containing lipid comprises:

TCO-LINK-LIPID wherein TCO is a trans-cyclooctene group, LINK is a bivalent linker, and LIPID is a lipid. In certain embodiments, TCO-LINK-LIPID is cell permeable.

In certain embodiments, TCO is selected from the group consisting of:

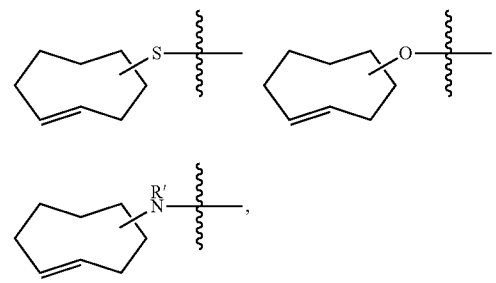

wherein R' is H or optionally substituted $C_1$-$C_6$ alkyl, and wherein the heteroatom is not attached to the ring double bond.

In certain embodiments, TCO is selected from the group consisting of:

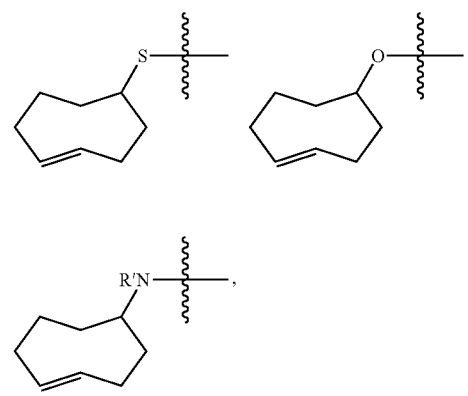

wherein R' is H or optionally substituted $C_1$-$C_6$ alkyl.

In certain embodiments, LIPID comprises a sphingolipid comprising a fatty acid. Fatty acids of any length and/or saturation are contemplated within the invention. In other embodiments, LIPID comprises a phospholipid, a glycerol lipid, a sterol lipid such as but not limited to cholesterol, and/or a fatty acid. In other embodiments, LIPID comprises at least one selected from the group consisting of sphingosine (also known as 2-amino-4-octadecene-1,3-diol), 1-phosphocholine-sphingosine, 1-phosphoethanolamine-sphingosine, a 1-glycosyl-sphingosine, a salt, solvate, stereoisomer, or any mixtures thereof, and any mixtures thereof. In yet other embodiments, LIPID comprises sphingosine, or a salt, solvate, stereoisomer, or any mixtures thereof.

In certain embodiments, LIPID is covalently conjugated to LINK through an amino group or hydroxyl group in LIPID. In other embodiments, LIPID is covalently conjugated to LINK through an amino group in LIPID. In yet other embodiments, LIPID comprises sphingosine and is covalently conjugated to LINK through the 2-amino group of sphingosine. In yet other embodiments, LIPID comprises sphingosine and is covalently conjugated to LINK through an amide group involving the 2-amino group of sphingosine and a carbonyl group in LINK.

In certain embodiment, LINK comprises an amino- or hydroxyl-substituted fatty acid. In other embodiments, LINK comprises:

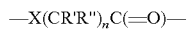

wherein X is covalently conjugated to TCO and is selected from the group consisting of a covalent bond, —C(=O)—, —C(=O)O— and —C(=O)NR'—; each occurrence of R' and R" is independently selected from the group consisting of H and optionally substituted $C_1$-$C_6$ alkyl; and n is an integer ranging from 1 to 20. In yet other embodiments, each occurrence of R' and R" is H. In yet other embodiments, n is 5.

In other embodiment, LINK comprises an amino- or hydroxyl-substituted acid, wherein the acid comprises $(CH_2CH_2O)_n$, wherein n is an integer ranging from 1 to 10. In yet other embodiments, LINK comprises:

wherein X is covalently conjugated to TCO and is selected from the group consisting of a covalent bond, —C(=O)—, —C(=O)O— and —C(=O)NR'—; R' is selected from the group consisting of H and optionally substituted $C_1$-$C_6$ alkyl; and n is an integer ranging from 1 to 10.

In certain embodiments, the trans-cyclooctene-containing lipid is Cer-TCO:

Cer-TCO

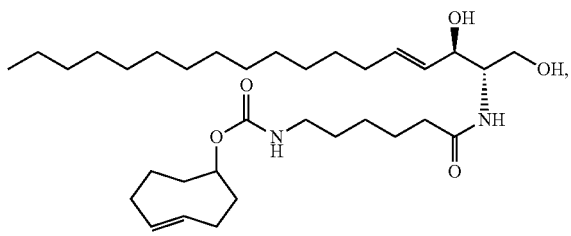

or a salt, solvate, stereoisomer, or any mixtures thereof.

The invention further provides a tetrazine-containing dye. In certain embodiments, the dye comprises the group:

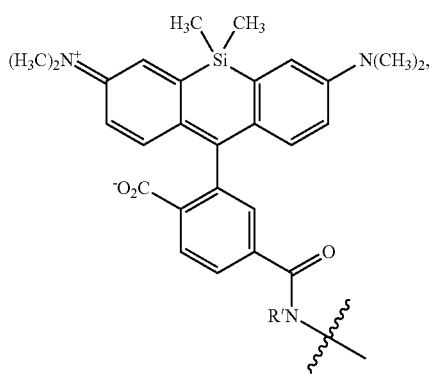

wherein R' is H or optionally substituted $C_1$-$C_6$ alkyl.

In certain embodiments, the dye further comprises the group:

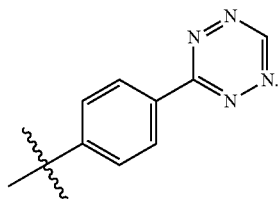 [SMILES: *c1ccc(-c2nncnn2)cc1]

In certain embodiments, the dye, or a salt, solvate, stereoisomer, or any mixtures thereof, is:

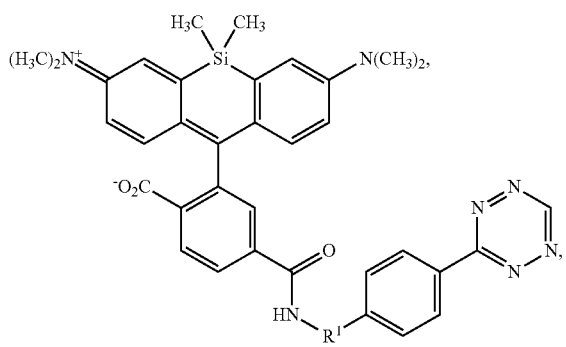

wherein
$R^1$ is —$(CH_2)_n$— or —$(CH_2CH_2O)_n(CH_2)_m$—; n is an integer ranging from 1 to 6; and m is 0, 1 or 2. In other embodiments, $R^1$ is —$(CH_2)$—.

In certain embodiments, the dye is SiR-Tz, or a salt, solvate, stereoisomer, or any mixtures thereof:

SiR-Tz

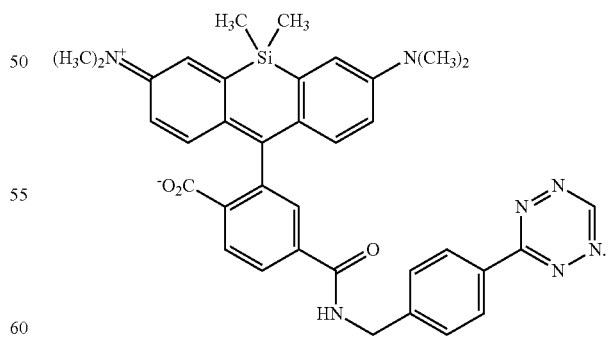

The invention further provides the cycloaddition product of the reaction between the trans-cyclooctene-containing lipid of the invention and the tetrazine-containing dye. In certain embodiments, the cycloaddition product, or a salt, solvate, stereoisomer, or any mixtures thereof, is:

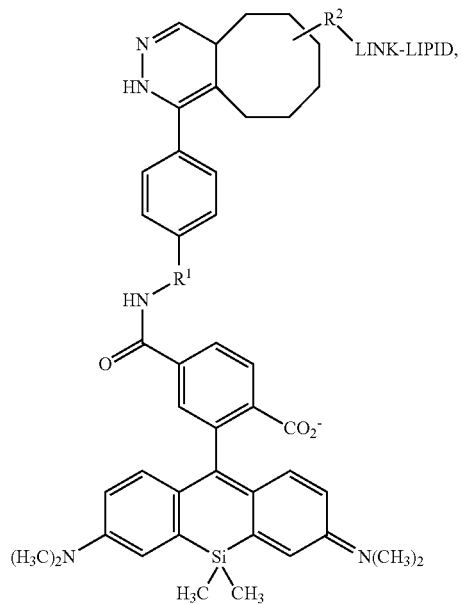

wherein in (I) $R^1$ is $-(CH_2)_n-$ or $-(CH_2CH_2O)_n(CH_2)_m-$; each occurrence of n is independently an integer ranging from 1 to 6; m is 0, 1 or 2; n is an integer ranging from 1 to 20; $R^2$ is S, O or NR'; LINK comprises $-X(CR'R'')_{1-20}C(=O)-$, wherein X is covalently conjugated to $R^2$ and is selected from the group consisting of a covalent bond, $-C(=O)-$, $-C(=O)O-$ and $-C(=O)NR'-$; LIPID comprises a sphingolipid; and, each occurrence of R' and R'' is independently selected from the group consisting of H and optionally substituted $C_1$-$C_6$ alkyl.

In certain embodiments, in (I) $R^1$ is $-CH_2-$. In other embodiments, in (I) $R^2$ is S, O or NH. In yet other embodiments, in (I) LINK is $-X(CH_2)_{1-20}C(=O)-$. In yet other embodiments, LINK is $-X(CH_2)_5C(=O)-$. In yet other embodiments, LINK is $-C(=O)NH(CH_2)_5C(=O)-$.

In certain embodiments, the cycloaddition product (I), or a salt, solvate, stereoisomer, or any mixtures thereof, is:

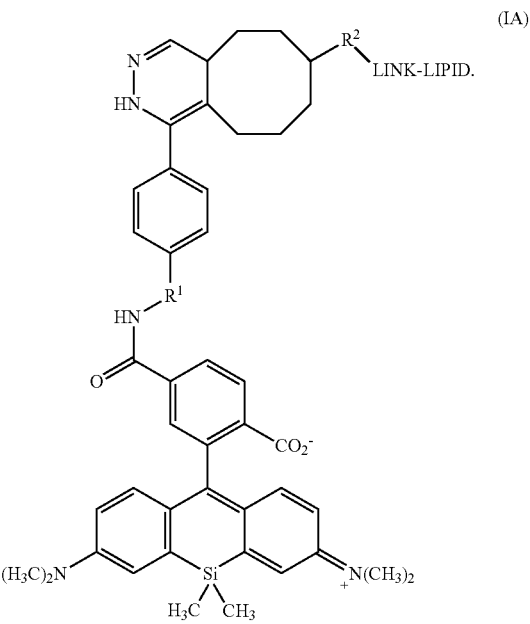

In certain embodiments, the cycloaddition product is Cer-SiR, or a salt, solvate, stereoisomer, or any mixtures thereof:

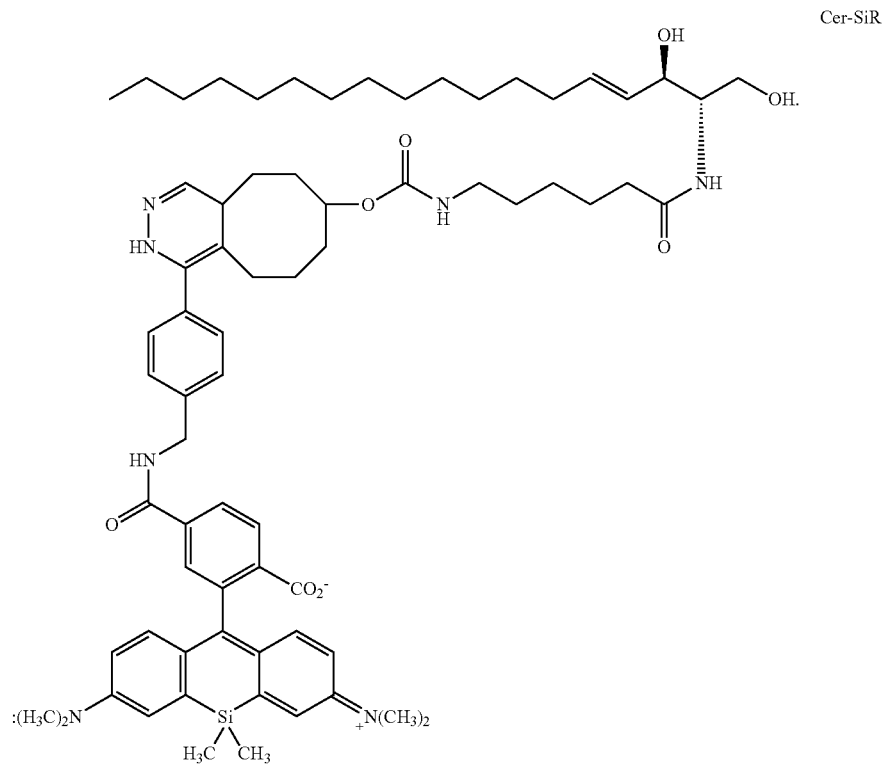

Cer-SiR

In certain embodiments, a compound of the invention is labelled with one or more isotopes, wherein one or more atoms is replaced by an atom having the same atomic number, but an atomic mass or mass number different from the atomic mass or mass number usually found in the non-labelled compound. Examples of isotopes suitable for inclusion in the compounds described herein include and are not limited to $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically labeled compounds are prepared by any suitable method or by processes using an appropriate isotopically labeled reagent in place of the non-labeled reagent otherwise employed.

The compounds of the invention may possess one or more stereocenters, and each stereocenter may exist independently in either the (R) or (S) configuration. In certain embodiments, compounds described herein are present in optically active or racemic forms. The compounds described herein encompass racemic, optically-active, regioisomeric and/or stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the compound described herein. In other embodiments, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with acceptable solvents such as water, and ethanol. In other embodiments, the compounds described herein exist in unsolvated form.

In certain embodiments, the compounds of the invention exist as tautomers. All tautomers are included within the scope of the compounds recited herein.

In certain embodiments, the compound of the invention is an acid addition salt. In other embodiments, the compound of the invention comprises an anion selected from the group consisting of chloride, bromide, iodide, nitrate, bicarbonate, sulfate, bisulfate, phosphate, hydrogen phosphate, dihydrogen phosphate, and aliphatic, cycloaliphatic, aromatic, araliphatic, heterocyclic, carboxylic and sulfonic classes of organic anions. Non-limiting examples of organic anions include, but are not limited to, formate, acetate, propionate, succinate, glycolate, gluconate, lactate, malate, tartrate, citrate, ascorbate, glucuronate, maleate, malonate, saccharinate, fumarate, pyruvate, aspartate, glutamate, benzoate, anthranilate, 4-hydroxybenzoate, phenylacetate, mandelate, embonate (pamoate), methanesulfonate, ethanesulfonate, benzenesulfonate, pantothenate, trifluoromethanesulfonate, 2-hydroxyethanesulfonate, p-toluenesulfonate, sulfanilate, cyclohexylaminosulfonate, stearate, alginate, β-hydroxybutyrate, salicylate, galactarate and galacturonate acid.

In certain embodiments, the compound of the invention is a base addition salt. In other embodiments, the compound of the invention comprises a metallic cation selected from the group consisting of an alkali metal, alkaline earth metal and transition metal cation, such as, for example, calcium, magnesium, potassium, sodium and zinc. In other embodiments, the compound of the invention comprises a cation that is a protonated form of a basic amine such as, for example, N,N'-dibenzylethylene-diamine, chloroprocaine, choline, diethanolamine, ethylenediamine, meglumine (N-methylglucamine) and procaine.

All of these salts may be prepared from the corresponding compound by reacting, for example, the appropriate acid or base with the compound.

Compounds described herein may be purchased from commercial sources, synthesized from compounds available from commercial sources, or prepared using procedures described herein. In certain embodiments, reactive groups on intermediates may be protected in order to avoid their unwanted participation in side reactions. Protecting groups are used to block some or all of the reactive moieties and prevent such groups from participating in chemical reactions until the protective group is removed. In certain embodiments, each protective group is removable by a different means. Protective groups that are cleaved under totally disparate reaction conditions fulfill the requirement of differential removal.

Methods

The invention includes a method of labeling an intracellular structure in a cell. In certain embodiments, the cell is in vitro, ex vivo and/or in vivo.

In certain embodiments, the method comprises contacting the cell with at least one trans-cyclooctene-containing lipid of the invention. In other embodiments, the cell is contacted with the at least one trans-cyclooctene-containing lipid for a period of time that allows for the lipid to associate with the intracellular structure. In yet other embodiments, the method further comprises contacting the cell with at least one tetrazine-containing dye. In yet other embodiments, the cell is contacted with the at least one tetrazine-containing dye for a period of time that allows for the tetrazine-containing dye to react with the at least one trans-cyclooctene-containing lipid, whereby a cycloaddition product is formed and labels the intracellular structure.

In certain embodiments, the intracellular structure is visualized using 3D confocal and/or STED super-resolution microscopies. In other embodiments, the cycloaddition product is photostable. In yet other embodiments, the cycloaddition product does not undergo significant photodegradation after the acquisition of at least 100, or at least 200, or at least 300, or at least 400 3D images.

In certain embodiments, the intracellular structure is visualized using single molecule switching (SMS) super-resolution imaging using a redox buffer (e.g., dSTORM or GSDIM).

In certain embodiments, the intracellular structure is visualized by using SMS super-resolution imaging, wherein the dye intrinsically switches between fluorescent and non-fluorescent states.

In certain embodiments, the intracellular structure comprises the Golgi and/or trans-Golgi network. In other embodiments, the tetrazine-containing dye, trans-cyclooctene-containing lipid and cycloaddition product do not have any measurable effect on cell morphology. In yet other embodiments, the tetrazine-containing dye, trans-cyclooctene-containing lipid and cycloaddition product do not have any measurable effect on mobility of a protein within the Golgi, or in cargo traffic from the ER through the Golgi and to the plasma membrane.

In certain embodiments, the tetrazine-containing dye is SirR-Tz, or a salt or solvate thereof. In other embodiments, the trans-cyclooctene-containing lipid is Cer-TCO, or a salt or solvate thereof. In yet other embodiments, the cycloaddition product is Cer-SiR, or a salt or solvate thereof.

Kits

The invention includes a kit comprising a tetrazine-containing dye, trans-cyclooctene-containing lipid, applicator, and instructional material for use thereof. In certain embodiments, the instructional material included in the kit comprises instructions for labeling an intracellular structure in a cell using the compositions of the invention. The instructional material recites the conditions under which the methods of the invention should be implemented. In certain embodiments, the kit further comprises reagents or materials that can be used to label an intracellular structure in a cell.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Materials & Methods

Materials and reagents were of the highest commercially available grade and were used without further purification. Reactions were monitored by thin layer chromatography using Merck silica gel 60 F254 plates. Reaction mixtures were visualized on TLC plates by UV irradiation or by treatment with $KMnO_4$ and $I_2$. Flash chromatography was performed with a Teledyne Isco CombiFlash Rf using pre-packed columns with RediSep Rf Silica (40-60 μm) or RediSep Rf Gold Silica (20-40 μm, spherical).

$^1$H and $^{13}$C NMR spectra were recorded on Bruker DPX 400 or 500 and Agilent MR2 400 or DD2 600 NMR spectrometers. Chemical shifts are reported in ppm using TMS or the residual peak from the NMR solvent were used as a reference.

Absorption measurements were performed on a Beckman Coulter DU 730 UV/vis spectrometer. Fluorescence measurements were performed on a Photon Technology international Fluorimeter.

UPLC and HR-LCMS were performed on a Waters Xevo Q-TOF LCMS with Electrospray Ionization using a Waters Acquity UPLC BEH300 C18 1.7 μm (186003686) or Acquity UPLC BEH300 C4 1.7 μm (186004496) column (solvent A: $H_2O$ with 0.1% formic acid; solvent B: MeCN with 0.1% formic acid). Semi-preparative HPLC was carried out on an Agilent 1260 Infinity instrument using a Vydac 219TP Diphenyl Column (250 mm×10 mm) column from Grace (solvent A: $H_2O$ with 1% MeCN and 0.1% TFA; solvent B: MeCN with 0.1% TFA).

Cell Culture and Imaging:

The following reagents were used for cell culture and preparation of samples for microscopy, with suppliers given in parentheses. Dulbecco's modified eagle's medium (DMEM) (high glucose) (Gibco), fetal bovine serum (FBS) (Sigma-Aldrich), phenol red-free DMEM (DMEM ph(−)) (Gibco), rabbit anti-green fluorescent protein (GFP) polyclonal antibody (life technology), mouse anti-GM130 monoclonal antibody (BD Transduction laboratories), goat anti-mouse IgG antibody tagged with Atto 647N (Sigma-Aldrich), goat anti-rabbit IgG antibody tagged with Alexa Fluor 568 (Invitrogen), casein (Sigma-Aldrich), paraformaldehyde (PFA) (Fluka), Pluronic F-127 (Sigma-Aldrich), BODIPY FL C5-Ceramide (BDP-Cer) (Invitrogen), Hoechst 33342 (Invitrogen), D/D-solubilizer (Clontech Laboratories, cat. no. 635054), Prolong Gold antifade reagent (Invitrogen).

SiR-BG was provided by K. Johnsson (EPFL, Switzerland). The preparation of the plasmid of TfRc-$F_M$-pH is described in Rivera-Molina, et al., 2013, J. Cell Biol. 201:673-680. HeLa cells stably expressing the GalNAc transferase T2-GFP fusion protein (GalNAcT2-GFP) were provided by B. Storrie (UAMS, USA) and the plasmid encoding the Rab6-SNAP-tag fusion protein (pRab6-SNAP) were received from J. Rothman (Yale University, School of Medicine, USA).

Spinning-disk confocal microscopy was performed using a Improvision UltraVIEW VoX system (Perkin-Elmer) built around a Nikon Ti-E inverted microscope, equipped with PlanApo objectives (60×1.45-NA) and controlled by the Volocity software (Improvision). Green, red and magenta channels correspond to the following filters: 527±23 nm, 615±35 nm, 705±45 nm.

Electroporation was performed with a Super Electroporator NEPA21 (Nepa Gene Co., Ltd).

Cell Culture and Transfection:

HeLa cells and HeLa cells stably expressing GalNAcT2-GFP were cultured in DMEM supplemented with 10% FBS, 100 unit/mL penicillin and 100 μg/mL streptomycin at 37° C. under an atmosphere of 5% (v/v) $CO_2$. Transfection of plasmid into the cells was performed with electroporation using the following two-step pulse-sequence: two 3 ms pulses with 50 ms intervals (125 V) as a poring pulse, and five 50 ms pulses with 50 ms intervals (25 V) as a transfer pulse.

Labeling and Confocal Microscopy (FIGS. 2A-2D):

Stably or transiently transfected HeLa cells were cultured on 35 mm glass bottom dishes (Mattek). To label with Cer-TCO/SiR-Tz, the cells were incubated in PBS containing 1% casein, 0.2% Pluronic F-127 and 2 or 5 µM TCO-Cer for 5 min at 37° C. After washing three times with DMEM ph(−), the cells were incubated for 1 h at 19.5° C. in DMEM ph(−). During this incubation the dish was sealed with parafilm to protect the cells from the used water bath. Subsequently, the cells were washed three times and PBS containing 1% casein and 2 or 1 µM SiR-Tz, respectively, was added to the dish. The dish was sealed with parafilm again and incubated for 30 min at 19.5° C. After washing three times with DMEM ph(−), the cells were observed under a confocal microscope. Fixed samples were prepared similarly with an additional treatment with 4% PFA for 10 min at room temperature after first temperature block. Then the cells were incubated in PBS containing 1% casein and 2 or 1 µM SiR-Tz, respectively, for 30 min at 37° C., and after washing, PBS was added to the dish. For SNAP-tag labeling, the cells transfected with SNAP-Rab6 by electroporation were incubated in PBS containing 1% casein and 5 µM SiR-BG for 1 hr at 37° C. The cells were washed three times, and incubated in DMEM ph(−) for 2-3 hr at 37° C. To obtain fixed samples the cells were treated with 4% PFA at this point. After washing the cells were observed under a confocal microscope. The labeling of the Golgi with BDP-Cer followed Pagano, et al., 1991, J. Cell Biol. 113:1267-1279.

Confocal microscopy was performed at 37° C. using a custom built incubation chamber. 488-nm and 640-nm laser lines were used to image GFP/BDP and SiR, respectively. 3D Images with a thickness of 12 µm to 14 µm and a pitch of 0.5 µm between each layer were taken and are shown as an extended focus in the figures. Images were typically sampled with an exposure time in the range of 150 to 300 ms.

Incubation with Premixed/Preassembled Cer-SiR

Using three different protocols, it was demonstrated that preassembled Cer-SiR is not suitable for Golgi labeling and that the two step (two component) approach is necessary (FIG. 15).

An approximately 2 µM solution of Cer-SiR was prepared as follows: Stock solutions in DMSO of SiR-Tz and Cer-TCO were added to a PBS buffer supplemented with 1% casein to achieve a final concentration of 2 µM for both components. The solution was thoroughly mixed and incubated for 15 min at room temperature. Before the solution was added to dishes containing cells, Pluronic F-127 was added (0.2% final concentration). The formation of Cer-SiR was confirmed by HPLC.

Protocol A: HeLa cells stably transfected to express GalNAcT2-GFP were cultured on 35 mm glass bottom dishes (Mattek), washed with DMEM (3×) and incubated with the Cer-SiR solution (prepared as described elsewhere herein) for 5 min at 37° C. The dish was washed with DMEM (3×) and incubated at 19.5° C. for 60 min, washed with DMEM (3×) and imaged.

Protocol B: Same as protocol A, but without the wash step before the incubation at 19.5° C.

Protocol C: HeLa cells stably transfected to express GalNAcT2-GFP were cultured on 35 mm glass bottom dishes (Mattek), washed with DMEM (3×) and incubated with the Cer-SiR solution described for 30 min at 4° C. The dish was washed with DMEM (3×) and incubated at 37° C. for 30 min, washed with DMEM (3×) and imaged. This protocol was similar to the protocol used for Golgi labeling with BODIPY-Cer.

Pearson Correlation

The Pearson correlation between the SiR and the GFP signal within cells was determined using the correlation measurement tool in Volocity. The automatic threshold function was activated. For cells stably expressing GalNAcT2-GFP and treated with SiR-Tz and Cer-TCO 13 samples (cells) were analyzed and for cells only treated with SiR-Tz 8 samples were analyzed. Pearson's analysis was performed only on the "Golgi" area (the weaker signal presumably due to the ER staining as excluded).

Immunofluorescence Analysis of Golgi Function (FIGS. 3A-3C):

Cells transfected with TfRc-$F_M$-pH were cultured on a cover glass. Three days after culture, the experiment was done. For the negative control and for the treatment with 5 µM TCOCer, the cells were incubated in PBS containing 1% casein with or without 0.2% pluronic and 5 µM TCO-Cer for 5 min at 37° C. After washing the cells, the dish was sealed with parafilm and incubated for 1 h at 19.5° C. For the treatment with 2 µM TCO-Cer and 2 µM SiR-Tz, the cells were labeled according to the protocol described elsewhere herein. After the temperature block, 2 µM solubilizer in DMEM ph(−) was added to the dishes in order to release TfRc-$F_M$-pH form the ER. One dish of each condition was fixed with 4% PFA for 10 min at RT as a time point of 0 min. The rest of the dishes was fixed with 4% PFA for 10 min at RT after 60 min of incubation at 37° C. (time point of 60 min). The cells were washed with PBS containing 5% BSA (blocking buffer) three times, and incubated in blocking buffer for 30 min at RT. Subsequently, the cells were incubated in blocking buffer with a 1:600 dilution of rabbit anti-GFP antibody (primary antibody) for 1 hour at RT with gentle shaking After washing three times with PBS containing 0.05% Tween 20 (washing buffer) for 5 min, the cells were fixed again with 4% PFA for 10 min at RT. Then, PBS with 0.1% Triton X was added to the dish, and the cells were incubated for 10 min at RT. After washing three times with washing buffer for 5 min (without shaking), the cells were incubated in blocking buffer with 1:600 dilution of mouse anti-GM130 antibody (second primary antibody) for 1 hour at RT with gentle shaking After washing three times with washing buffer for 5 min, the cells were incubated in blocking buffer with two secondary antibodies, namely a 1:800 dilution of goat anti-rabbit IgG antibody tagged with Alexa Fluoro 568 and goat anti-mouse IgG antibody tagged with Atto 647N and 1 µg/mL Hoechst for 30 min at RT with gentle shaking. The cells were washed three times with washing buffer for 5 min, once with PBS and once with water. The cells were cured on a cover glass with Prolong. The cells were observed under a confocal microscope. 405-nm, 488-nm, 560-nm and 647-nm laser lines were used to image Hoechst, GFP, Alexa Fluoro 568 and Atto 647N, respectively. Images of multiple Z positions in 12 µm thick stacks were taken every 1 µm with exposure times of 900 ms, 300 ms, 250 ms and 500 ms for 405-nm, 488-nm, 560-nm and 647-nm laser lines, respectively. The images were analyzed by ImageJ and are shown as an extended focus in FIG. 3B. For the image analysis the mean intensities of green and red fluorescence in the background were subtracted from those of whole cells. The obtained values were multiplied by the area of whole cell to obtain the absolute fluorescence of a whole cell. The absolute value for green fluorescence represents the total amount of TfRc-$F_M$- pH inside and outside of a cell. The absolute value for red fluorescence represents the amount of TfRc-$F_M$-pH on the plasma membrane. Red-to-green ratios were calculated to consider differences in size and expression levels of TfRc-$F_M$-pH between different cells. 26-38 cells were analyzed for each condition. Red and green signal of individual cells are show in FIG. 9. Cells with a GFP expression level over 3× the standard deviation of an average cell were excluded. Specifically, this corresponds to cells with a total GFP signal above 1,000,000 AU. Two or fewer cells were excluded from each experiment.

FRAP Analysis (FIGS. 4A-4C):

The stable cell line was cultured on a 35 mm glass bottom dish. In the negative control (no treatment), the medium was replaced by DMEM ph(−). For the condition with only the temperature block, the dish was sealed with parafilm and incubated in DMEM ph(−) for 1 hr at 19.5° C. in a water bath. After washing three times, DMEM ph(−) was added to the dish. For the condition with the temperature block and TCO-Cer treatment, the cells were incubated in PBS containing 1% casein, 0.2% pluronic and 5 µM TCO-Cer for 5 min at 37° C. Then the cells were washed three time and incubated in DMEM ph(−) for 1 hr at 19.5° C. After washing three times DMEM ph(−) was added to the dish. For the condition with the temperature block, and TCO-Cer (5 µM) and SiR-Tz (1 µM) treatment the protocol described elsewhere herein was used. The photobleaching of the FRAP experiment was performed with a fluorescence recovery after photobleaching unit of the microscope. A region of interest was bleached with 20 bleaching cycles using 100% laser power of 488-nm laser line. Images at multiple Z-positions of 13 µm thick stacks were taken every 1 µm at 0.1 Hz with an exposure time of 120 ms. Quantification was performed with ImageJ. The fluorescence intensity in the unbleached region of the cytosol was subtracted from that in the bleached region of Golgi. The obtained intensity values were normalized to an initial value. Mean values of 9 cells are illustrated in FIG. 4C.

Cell Viability (FIG. 4D):

Hela cells stably expressing GalNAcT2-GFP were cultured on 35 mm glass bottom dishes subsequently labeled with various concentrations of TCO-Cer (0, 1, 2, and 5 µM) and SiR-Tz (0, 1, and 2 µM) following the protocol described elsewhere herein. For the labeling BDP-Cer, Hela cells were labeled according to the manufacturer's instructions. The dishes containing the labeled cells covered with 2 ml DMEM ph(−) were sealed with Parafilm™ and placed on the stage of a scanning disc confocal microscope set to 37° C. (using a custom built incubation chamber). After equilibration for 30 min, phase contrast images were taken at an interval of 20 min and fluorescence images at an interval of 10 min over 400-750 min. Between 10 and 12 fields of view were imaged for each sample. The number of physically intact cells was counted at each time point. For each condition at least 110 cells were counted/observed in the initial images ($n_0$ (0 µM TCO-Cer, 0 µM SiR-Tz)=123 cells, $n_0$ (2 µM TCO-Cer, 2 µM SiR-Tz)=113 cells, $n_0$ (1 µM TCO-Cer, 1 µM SiR-Tz)=130 cells, $n_0$ (5 µM TCO-Cer, 1 µM SiR-Tz)=120 cells, $n_0$ (5 µM BODIPY-Cer)=123 cells).

STED Microscopy (FIG. 6A):

The stable cell line was cultured on 35 mm glass bottom dish. The cells were labeled following the protocols described elsewhere herein.

STED imaging was carried out on a commercially available Leica TCS STED microscope. A picosecond pulsed laser diode (PicoQuant, LDH-P-F-640B) was used for excitation while depletion was achieved with a femtosecond pulsed mode-locked Ti:Sapphire laser (Spectra Physics, Mai Tai) tuned to 755 nm with the output pulses stretched to approximately 200 ps via propagation through a 120 meter single mode polarization maintaining fiber. The excitation and depletion beams were directed into a 100×1.4NA oil immersion objective (Leica) which also collected fluorescence from the sample. Fluorescence was filtered from excitation light with a band pass filter (Semrock, FF01-685/40) and detected with an avalanche photodiode. The FWHM values of the intensity line profiles were obtained by fitting them to a Lorentz distribution using Origin 9.1 (www dot originlab dot com).

STED Microscopy (FIGS. 6B-6C):

STED imaging was performed on a custom built system (Bewersdorf lab, Yale University) centered around an 80 MHz mode-locked Ti:Sapphhire laser (Chameleon Ultra II, Coherent) tuned to 755 nm as the STED depletion beam. The output pulses from the depletion laser were stretched to several hundred picoseconds by first passing through a glass block made from a high dispersion material (SF6, Schott) and then coupled into a 100 m polarization-maintaining single mode optical fiber. After leaving the optical fiber the depletion beam was collimated and directed onto an SLM, conjugate to the objective back pupil plane, where a 2π phase ramp was displayed. Excitation for fluorescence was accomplished with a 640 nm pulsed diode laser (PicoQuant) electronically synchronized to the depletion beam with an additional computer controlled electronic delay (Colby Instruments). The STED depletion and fluorescence excitation beams were combined with a dichroic mirror and directed into a 100×1.4 NA oil immersion objective lens (UPLSAPO 100XO/PSF, Olympus) where they were focused at the sample. A 16 kHz resonance scanning mirror, in combination with a galvanometer mirror, allowed imaging via beam scanning. The two mirrors were imaged into the objective pupil plane and allowed the beams to scan through the sample at a rate of 16 kHz along the fast axis.

Fluorescence from the sample was collected by the objective lens, de-scanned by the scan mirrors, and separated from the excitation and depletion light using dichroic mirrors and band pass filters (FF01-685/40, Semrock). The fluorescence was then focused into a 105 µm core (about 0.7 Airy units) multimode fiber connected to a single photon counting avalanche photodiode (ARQ-13-FC, Perkin Elmer). Counts from the APD were collected using an FPGA based data acquisition card (PCIe-7852R, National Instruments) and custom acquisition software (LabVIEW, National Instruments). Data collection was synchronized with the resonance mirror for uni-directional collection during the two-thirds of the half period where the motion of the mirror is most linear. Recorded pixel values were therefore linearized (on the DAQ card) to account for the sinusoidal velocity profile of the resonant mirror and normalized according the pixel dwell times such that the center pixel was divided by unity.

Imaging of fixed Cer-SiR labeled cells (FIG. 6B) was achieved with 640 nm excitation, 30 nm pixel size, a 512 by 512 image format, 755 nm STED laser, and 60 accumulations per line for resulting in a frame rate of 0.52 Hz. Imaging of live Cer-SiR labeled cells (FIG. 6C) was achieved with 640 nm excitation, 40 nm pixel size, a 512 by 512 image format, 755 nm STED laser, and 120 accumulations per line for resulting in a frame rate of 0.26 Hz. For improved presentation in FIG. 6C, the raw microscopy data were Gaussian blurred (0.75 pixels) in ImageJ.

Figure 7:
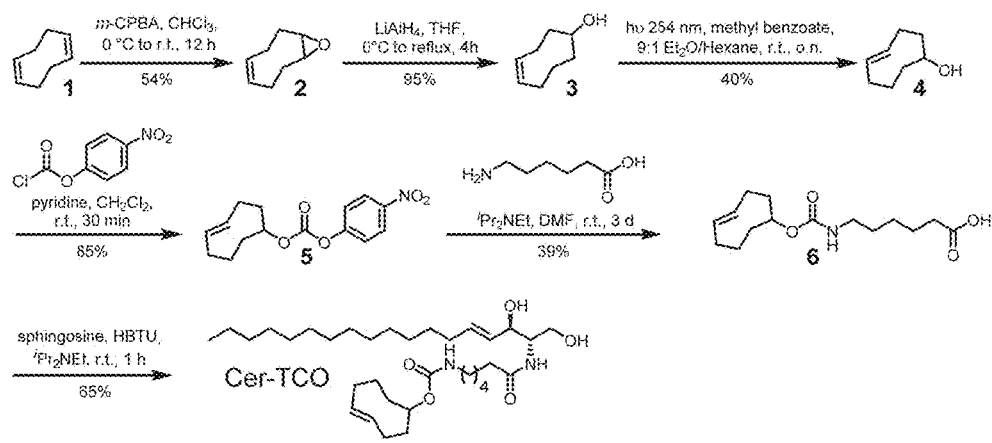
FIG. 7 is a schematic illustration of a synthetic route to Cer-TCO.

Example 1: Synthesis of Cer-TCO (FIG. 7)

Cis-1,5-cyclooctadiene 1 was converted to cyclooctene monoepoxide 2 with m-CPBA (Clark, et al., 2010, J. Am.

Chem. Soc. 132:3405-3412). The monoepoxide was reduced with LiAlH$_4$ to the alcohol 3 (Clark, et al., 2010, J. Am. Chem. Soc. 132:3405-3412). Cis-cyclooctenol 3 was isomerized to trans-cyclooctenol 4 according to Royzen, et al., 2008, J. Am. Chem. Soc. 130:3760-3761. From TCO 4 the corresponding p-nitrophenol carbonate 5 was prepared (Liu, et al., 2012, J. Am. Chem. Soc. 134:792-795).

Synthesis of rel-(1R-4E-pR)-cyclooct-4-ene-1-yl-N-hexanoic acid carbamate (6)

Carbonate 5 (100 mg, 343 μmol, 1.0 eq) and 6-aminohexanoic acid (135 mg, 1.03 mmol, 3.0 eq) were suspended in DMF (3 mL) and iPr$_2$NEt (360 μL, 2.06 mmol, 6.0 eq) was added. The suspension was stirred for 3 days. The volume of the reaction mixture was reduced to a minimum in vacuum. The residue was dissolved in 20 mL CH$_2$Cl$_2$ and washed with 1 M HCl (3×5 mL). The combined aqueous layers were extracted with CH$_2$Cl$_2$ (2×5 mL). The combined organic layers were dried over MgSO$_4$ and concentrated under reduced pressure. The residue was purified by column chromatography (0% to 5% MeOH in CH$_2$Cl$_2$). The title compound was obtained as 37.9 mg of a colorless oil (39%).

$^1$H NMR (400 MHz, MeOD-d$_3$) δ(ppm) 5.66-5.54 (m, 1H), 5.47 (ddd, J=16.0, 10.7, 3.5 Hz, 1H), 4.39-4.25 (m, 1H), 3.06 (t, J=7.0 Hz, 2H), 2.37-2.31 (m, 3H), 2.28 (t, J=7.4 Hz, 2H), 2.04-1.86 (m, 4H), 1.79-1.65 (m, 2H), 1.65-1.54 (m, 3H), 1.54-1.44 (m, 2H), 1.39-1.27 (m, 2H).

$^{13}$C NMR (101 MHz, MeOD-d$_3$) δ 177.4, 158.6, 136.0, 133.7, 81.5, 42.2, 41.5, 39.6, 35.2, 34.8, 33.5, 32.1, 30.6, 27.3, 25.7.

HRMS (ESI): m/z calc. for C$_{15}$H$_{26}$NO$_4^+$: 284.1856. found: 284.1857 (Δ=0.4 ppm).

Synthesis of Cer-TCO (7):

HBTU (40.1 mg, 77.1 μmol, 1.2 eq) were dissolved in DMF (0.8 mL) and iPr$_2$NEt (33.7 μL, 193 μmol, 3.0 eq) was added. This solution was added to TCO-acid 6 (18.2 mg, 64.2 μmol, 1.0 eq) and stirred for 2 min. Sphingosine (25.0 mg, 83.5 μmol, 1.3 eq) was added and the reaction mixture was diluted with DMF to a total volume of 2 mL. The mixture was stirred for 2.5 h and concentrated under reduced pressure. The yellow-brownish residue was purified by flash chromatography (0% to 5% MeOH in CH$_2$Cl$_2$, silica gel). A colorless oil was obtained which was dissolved in CH$_2$Cl$_2$ (50 mL) and washed with sat. NaHCO$_3$ (3×10 mL) and 1 M HCl (3×10 mL). The combined aqueous layers (one acidic, one basic) were extracted with CH$_2$Cl$_2$ (1×10 mL each). The combined organic layers were dried over MgSO$_4$, concentrated under reduced pressure and subjected to column chromatography (0% to 5% to 10% MeOH in CH$_2$Cl$_2$). The title compound was obtained as 23.6 mg of a colorless oil (65%).

$^1$H NMR (500 MHz, MeOD-d$_3$): δ(ppm) 5.72 (dt, J=14.3, 6.7 Hz, 1H), 5.68-5.56 (m, 1H), 5.54-5.44 (m, 2H), 4.42-4.27 (m, 1H), 4.09 (t, J=7.2 Hz, 1H), 3.89 (q, J=5.8 Hz, 1H), 3.71 (d, J=5.0 Hz, 2H), 3.08 (t, J=6.8 Hz, 2H), 2.42-2.29 (m, 3H), 2.23 (t, J=7.5 Hz, 2H), 2.06 (q, J=7.1 Hz, 2H), 2.03-1.89 (m, 4H), 1.81-1.68 (m, 2H), 1.68-1.56 (m, 3H), 1.50 (p, J=7.3 Hz, 2H), 1.31 (s, 23H), 0.92 (t, J=6.7 Hz, 3H).

$^{13}$C NMR (126 MHz, MeOD-d$_3$): δ (ppm) 176.5, 159.1, 136.5, 135.1, 134.2, 131.6, 81.9, 74.1, 62.7, 57.2, 42.7, 41.9, 40.1, 37.6, 35.6, 33.9, 33.8, 33.5, 32.6, 31.2, 31.2, 31.1, 30.9, 30.8, 30.8, 27.9, 27.1, 24.2, 14.9.

HRMS (ESI): m/z calc. for C$_{33}$H$_{61}$N$_2$O$_5^+$: 565.4575. found: 565.4563 (Δ=-2.1 ppm).

Figure 8:
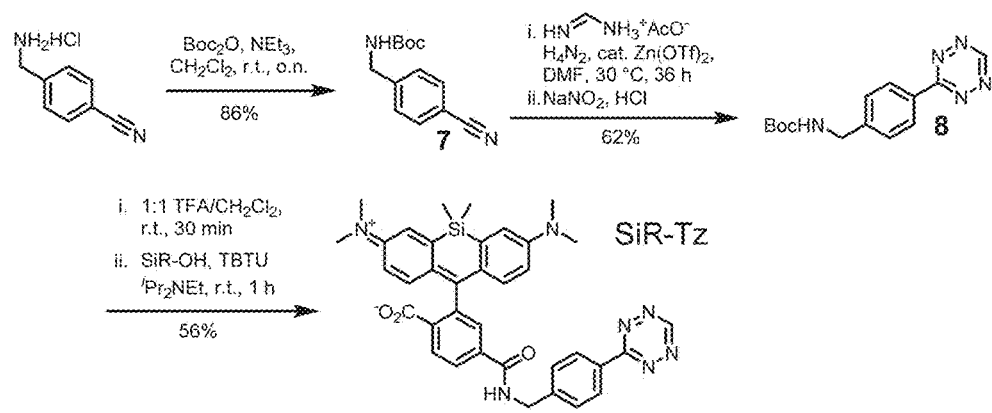
FIG. 8 is a schematic illustration of a synthetic route to SiR-Tz.

Example 2: Synthesis of SiR-Tz (FIG. 8)

4-Cyanobenzylamine HCl was Boc-protected with Boc-anhydride. The Boc-protected amine was converted to the tetrazine 8 (Yang, et al., 2012, Angew. Chem., Int. Ed. 51:5222-5225). The Boc-group of tetrazine 8 was removed by treating the compound with a 1:1 mixture of TFA and dichloromethane and immediately coupled with SiR—OH (Lukinavicius, et al., 2013, Nature Chem. 5:132-139) mediated by TBTU and iPr$_2$NEt.

Synthesis of tert-butyl(4-cyanobenzyl)carbamate (7)

4-Cyanobenzylamine HCl (5.00 g, 29.7 mmol, 1.0 eq) was suspended in CH$_2$Cl$_2$ and NEt$_3$ (10.3 mL, 74.1 mmol, 2.5 eq) were added to obtain a clear solution. Boc$_2$O (8.86 mL, 38.6 mmol, 1.3 eq) was added and the solution was stirred overnight. The reaction mixture was diluted to a total volume of 100 mL with CH$_2$Cl$_2$ and washed with 1 M HCl (3×15 mL) and sat. NaHCO$_3$ (3×15 mL). The organic layer was dried over MgSO$_4$ and concentrated under reduced pressure.

$^1$H NMR (500 MHz, CDCl$_3$) δ 7.58-7.52 (m, 2H), 7.35-7.29 (m, 2H), 4.88 (s, 1H), 4.30 (d, J=6.3 Hz, 2H), 1.39 (s, 9H).

$^{13}$C NMR (126 MHz, CDCl$_3$) δ 156.2, 145.0, 132.8, 128.2, 119.1, 111.6, 80.5, 44.6, 28.8.

HRMS (ESI): m/z calc. for C$_{13}$H$_{16}$N$_2$NaO$^{2+}$: 255.1104. found: 255.1110 (Δ=-2.0 ppm).

Synthesis of Sir-Tz:

The Boc-protected tetrazine 8 (18.3 mg, 63.5 μmol, 1.4 eq) was dissolved in CH$_2$Cl$_2$ (300 μL). This solution was added to a mixture of 1.0 ml TFA in 3.0 mL CH$_2$Cl$_2$. The reaction mixture was stirred for 30 mins and the progress of the reaction was monitored by TLC. After completion of the reaction the mixture was concentrated under reduced pressure without heating above 30° C. To the red residue a solution of TSTU (16.7 mg, 55.5 μmol, 1.2 eq) and iPr$_2$NEt (36.9 μl, 212 μmol, 4.7 eq) and Sir-OH (21.4 mg, 45.2 μmol, 1.0 eq) in DMSO (200 μl) was added (pre-stirred for 5 min). After 1 h 100 μL iPr$_2$NEt and 500 μL 2M iPr$_2$NEt in NMP were added and the blue solution was stirred for another 15 mins and then subjected to RPHPLC. The title compound was obtained as 15.3 mg of a blue solid (56%).

$^1$H NMR (600 MHz, acetone-d$_6$): δ(ppm) 10.42 (s, 1H), 8.50 (dd, J=8.3, 1.8 Hz, 2H), 8.22 (dd, J=8.0, 1.4 Hz, 1H), 7.87-7.85 (m, 1H), 7.64 (dd, J=8.3, 1.8 Hz, 2H), 7.17 (d, J=2.9, 2H), 6.80 (d, J=8.9 Hz, 2H), 6.70 (dd, J=8.9, 2.9 Hz, 2H), 4.71 (s, 2H), 2.99 (s, 12H), 0.68 (s, 3H), 0.56 (s, 3H).

$^{13}$C NMR (151 MHz, acetone-d$_6$): δ(ppm) 170.0, 167.0, 166.3, 159.0, 150.4, 145.5, 140.8, 137.6, 132.7, 132.0, 129.5, 129.4, 129.3, 129.0, 128.9, 126.4, 124.3, 118.0, 114.9, 43.9, 40.5, 0.2, -1.1.

HRMS (ESI): m/z calc. for C$_{36}$H$_{36}$N$_7$O$_3$Si$^+$: 642.2643. found: 642.2628 (Δ=-2.0 ppm).

UPLC: t$_R$=1.86 min; gradient: 0 min: 5% B, 1 min: 5% B, 1.6 min 95% B, 3.0 min: 95% B; C18 column).

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A trans-cyclooctene-containing lipid, or a salt, solvate, stereoisomer, or any mixtures thereof, wherein the lipid comprises TCO-LINK-LIPID, wherein TCO is a trans-cyclooctene group, LINK is a bivalent linker, and wherein LIPID comprises at least one selected from the group consisting of a sphingolipid, phospholipid, sterol lipid and fatty acid wherein LINK comprises:

—X(CR'R")$_n$C(=O)—, wherein

X is covalently conjugated to TCO and is selected from the group consisting of a covalent bond, —C(=O)—, —C(=O)O— and —C(=O)NR'—;

each occurrence of R' and R" is independently selected from the group consisting of H and optionally substituted $C_1$-$C_6$ alkyl; and n is an integer ranging from 1 to 20.

2. The trans-cyclooctene-containing lipid of claim 1, wherein TCO is selected from the group consisting of:

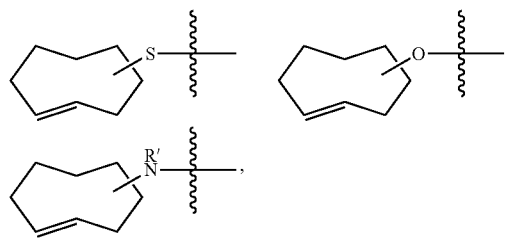

wherein R' is H or optionally substituted $C_1$-$C_6$ alkyl, and wherein the heteroatom is not attached to the ring double bond.

3. The trans-cyclooctene-containing lipid of claim 2, wherein TCO is selected from the group consisting of:

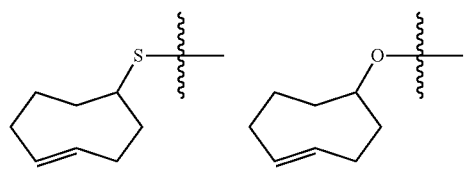

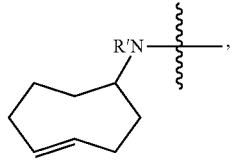

wherein R' is H or optionally substituted $C_1$-$C_6$ alkyl.

4. The trans-cyclooctene-containing lipid of claim 1, wherein LIPID comprises at least one selected from the group consisting of sphingosine, 1-phosphocholine-sphingosine, 1-phosphoethanolamine-sphingosine, and a 1-glycosyl-sphingosine.

5. The trans-cyclooctene-containing lipid of claim 4, wherein LIPID comprises sphingosine.

6. The trans-cyclooctene-containing lipid of claim 5, wherein LIPID comprises sphingosine and is covalently conjugated to LINK through the 2-amino group of sphingosine.

7. The trans-cyclooctene-containing lipid of claim 1, wherein n is 5.

8. The trans-cyclooctene-containing lipid of claim 1, which is Cer-TCO or a salt, solvate, stereoisomer, or any mixtures thereof:

Cer-TCO

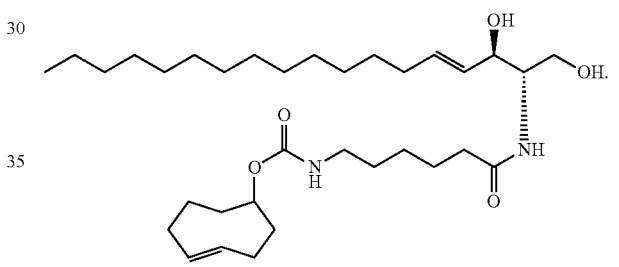

* * * * *